US012662671B2

(12) United States Patent
Wei et al.

(10) Patent No.: US 12,662,671 B2
(45) Date of Patent: Jun. 23, 2026

(54) CONSTRUCTS AND METHODS FOR PREPARING CIRCULAR RNA

(71) Applicant: Peking University, Beijing (CN)

(72) Inventors: Wensheng Wei, Beijing (CN); Zongyi Yi, Beijing (CN)

(73) Assignee: PEKING UNIVERSITY (CN)

( * ) Notice: Subject to any disclaimer, the term of this patent is extended or adjusted under 35 U.S.C. 154(b) by 42 days.

(21) Appl. No.: 18/587,710

(22) Filed: Feb. 26, 2024

(65) Prior Publication Data

US 2024/0247265 A1     Jul. 25, 2024

Related U.S. Application Data

(63) Continuation of application No. PCT/CN2022/082225, filed on Mar. 22, 2022.

(30) Foreign Application Priority Data

Aug. 27, 2021    (WO) ................ PCT/CN2021/115029

(51) Int. Cl.
*C12N 15/52*        (2006.01)
*C12N 15/113*       (2010.01)

(52) U.S. Cl.
CPC ............ *C12N 15/113* (2013.01); *C12N 15/52* (2013.01); *C12N 2770/32343* (2013.01)

(58) Field of Classification Search
CPC ........ C12N 15/85; C12N 15/113; C12N 9/93; C12N 2770/32343; C12N 2840/203; C12Y 605/01003; C12P 19/34; A61K 48/0066
See application file for complete search history.

(56) References Cited

U.S. PATENT DOCUMENTS 5,766,903  A     6/1998  Sarnow et al.
8,241,610  B2    8/2012  Agger et al.
(Continued)

FOREIGN PATENT DOCUMENTS

CN        108165549 A     6/2018
CN        108251424 A     7/2018
(Continued)

OTHER PUBLICATIONS

Qu et al. (Cell vol. 185, pp. 1728-1744, May 12, 2022).*
(Continued)

*Primary Examiner* — Terra C Gibbs
(74) *Attorney, Agent, or Firm* — MORRISON & FOERSTER LLP

(57)     ABSTRACT

The present application provides linear RNA precursors and constructs for preparing circular RNAs (circRNAs) comprising an effector RNA sequence, such as a coding RNA sequence. In some embodiments, the linear RNA comprises from the 5' end to the 3' end: (a) a first portion of an RNA element (e.g., an IRES), (b) an effector RNA sequence, and (c) a second portion of the RNA element, wherein the first and the second portions of the RNA element associate with each other to form a double-stranded region of at least 4 basepairs long, wherein 5' end of the first portion of the RNA element and 3' end of the second portion of the RNA element form a nick in the double-stranded region, and wherein an RNA ligase can ligate the nick. Also provided are methods of preparing circRNAs, circRNAs prepared thereof, and methods of using the circRNAs.

19 Claims, 8 Drawing Sheets

Specification includes a Sequence Listing.

(56) References Cited

U.S. PATENT DOCUMENTS

| | | | |
|---|---|---|---|
| 8,399,007 | B2 | 3/2013 | Taft et al. |
| 8,506,966 | B2 | 8/2013 | Podda et al. |
| 8,603,457 | B2 | 12/2013 | Yu |
| 10,407,683 | B2 * | 9/2019 | Nelson .................. C07H 21/02 |
| 11,981,909 | B2 * | 5/2024 | Anderson .............. C12N 15/11 |
| 2010/0137407 | A1 | 6/2010 | Abe et al. |
| 2010/0303850 | A1 | 12/2010 | Lipford et al. |
| 2011/0293700 | A1 | 12/2011 | Bratzler et al. |
| 2011/0293701 | A1 | 12/2011 | Bratzler et al. |
| 2011/0293723 | A1 | 12/2011 | Bratzler et al. |
| 2012/0027806 | A1 | 2/2012 | Ilyinskii et al. |
| 2012/0027813 | A1 | 2/2012 | Podda et al. |
| 2019/0022247 | A1 | 1/2019 | Ansell et al. |
| 2020/0080106 | A1 | 3/2020 | Anderson et al. |
| 2020/0121809 | A1 | 4/2020 | Hope et al. |
| 2020/0163878 | A1 | 5/2020 | Baumhof et al. |
| 2022/0135963 | A1 | 5/2022 | Wei et al. |
| 2022/0177908 | A1 | 6/2022 | Sun et al. |
| 2023/0346921 | A1 | 11/2023 | Wei |
| 2025/0051816 | A1 | 2/2025 | Wei et al. |
| 2025/0082746 | A1 | 3/2025 | Wei et al. |
| 2025/0108134 | A1 | 4/2025 | Wei et al. |

FOREIGN PATENT DOCUMENTS

| | | | | |
|---|---|---|---|---|
| CN | 109554368 | A | 4/2019 | |
| CN | 109666744 | B | 10/2019 | |
| CN | 111057764 | A | 4/2020 | |
| CN | 111217917 | A | 6/2020 | |
| CN | 111321143 | * | 6/2020 | ........... C12N 15/113 |
| CN | 111321143 | A | 6/2020 | |
| CN | 111378686 | A | 7/2020 | |
| CN | 112574997 | A | 3/2021 | |
| CN | 112725378 | A | 4/2021 | |
| WO | 2010138192 | A2 | 12/2010 | |
| WO | 2010138192 | A3 | 6/2011 | |
| WO | 2011068810 | A1 | 6/2011 | |
| WO | 2011150240 | A1 | 12/2011 | |
| WO | 2011150249 | A1 | 12/2011 | |
| WO | 2011150258 | A1 | 12/2011 | |
| WO | 2011150264 | A2 | 12/2011 | |
| WO | 2012170930 | A1 | 12/2012 | |
| WO | 2011150264 | A3 | 4/2013 | |
| WO | 2016197121 | A1 | 12/2016 | |
| WO | 2017222911 | A1 | 12/2017 | |
| WO | 2018237372 | A1 | 12/2018 | |
| WO | 2019008001 | A1 | 1/2019 | |
| WO | 2019/094486 | A1 | 5/2019 | |
| WO | 2019118919 | A1 | 6/2019 | |
| WO | 2019189722 | A1 | 10/2019 | |
| WO | 2019223293 | A1 | 11/2019 | |
| WO | 2019236673 | A1 | 12/2019 | |
| WO | 2020181013 | A1 | 9/2020 | |
| WO | 2020237227 | A1 | 11/2020 | |
| WO | 2021008447 | A1 | 1/2021 | |
| WO | 2021030701 | A1 | 2/2021 | |
| WO | 2021156267 | A1 | 8/2021 | |
| WO | 2021196268 | A1 | 10/2021 | |
| WO | 2021236855 | A1 | 11/2021 | |
| WO | 2022037692 | A1 | 2/2022 | |
| WO | 2022088953 | A1 | 5/2022 | |
| WO | 2022105825 | A1 | 5/2022 | |
| WO | 2022150974 | A1 | 7/2022 | |
| WO | 2022261490 | A2 | 12/2022 | |
| WO | 2023020574 | A1 | 2/2023 | |
| WO | 2023115732 | A1 | 6/2023 | |
| WO | 2023133684 | A1 | 7/2023 | |
| WO | 2023134611 | A1 | 7/2023 | |
| WO | 2023143541 | A1 | 8/2023 | |

OTHER PUBLICATIONS

Bai Y. et al. (2023) (Front. Immunol. 13:1091797. doi: 10.3389/fimmu.2022.1091797).*

Accession ID: EPI-ISL-402124. (2019). Abstract, 2 pages.

Bangaru, S. et al. (Nov. 27, 2020). "Structural Analysis of Full-Length SARS-CoV-2 Spike Protein from an Advanced Vaccine Candidate," Science 370:1089-1094.

Boutros, C. et al. (Aug. 2016, e-pub. May 4, 2016). "Safety Profiles of Anti-CTLA-4 and Anti-PD-1 Antibodies Alone and in Combination," Nat. Rev. Clin. Oncol. 13:473-486.

Bouwman, K.M. et al. (Feb. 8, 2021). "Multimerization- and Glycosylation-Dependent Receptor Binding of SARS-CoV-2 Spike Proteins," PLoS Pathog. 17:e1009282, 20 pages.

Cao, Y. et al. (Jul. 9, 2020). "Potent Neutralizing Antibodies Against SARS-CoV-2 Identified By High-Throughput Single-Cell Sequencing of Convalescent Patients' B Cells," Cell 182:73-84, 29 pages.

Cele, S. et al. (May 2021). "Escape of SARS-CoV-2 501Y.V2 from Neutralization by Convalescent Plasma," Nature 593(7857):142-146, 24 pages.

Chan, K. K. et al. (Sep. 4, 2020). "Engineering Human ACE2 to Optimize Binding to the Spike Protein of SARS Coronavirus 2," Science 369:1261-1265.

Chen, L.L. (Apr. 2016, e-pub. Feb. 24, 2016). "The Biogenesis and Emerging Roles of Circular RNAs," Nat. Rev. Mol. Cell Biol. 17(4):205-211, 7 pages.

Chen, R. E. et al. (Apr. 2021). "Resistance of SARS-CoV-2 Variants to Neutralization by Monoclonal and Serum-Derived Polyclonal Antibodies," Nat. Med. 27(4):717-726, 35 pages.

Chen, Y.G. et al. (Oct. 3, 2019). "N6-Methyladenosine Modification Controls Circular RNA Immunity," Mol. Cell 76(1):96-109, 42 pages.

Corbett, K.S. et al. (Jul. 28, 2020). "Evaluation of the mRNA-1273 Vaccine Against SARS-CoV-2 in Nonhuman Primates," N. Engl. J. Med. 383:1544-1555.

Corbett, K.S. et al. (Oct. 2020). "SARS-CoV-2 mRNA Vaccine Design Enabled by Prototype Pathogen Preparedness," Nature 586(7830):567-571, 26 pages.

Dai, L. et al. (Aug. 6, 2020). "A Universal Design of Betacoronavirus Vaccines against COVID-19, MERS, and SARS," Cell 182:722-733, 24 pages.

Davies, N. G. et al. (2021). "Increased Hazard of Death in Community-Tested Cases of SARS-CoV-2 Variant of Concern 202012/01," medRxiv, 49 pages.

Du, S. et al. (Nov. 12, 2020). "Structurally Resolved SARS-CoV-2 Antibody Shows High Efficacy in Severely Infected Hamsters and Provides a Potent Cocktail Pairing Strategy," Cell 183:1013-1023, 26 pages.

Durymanov, M. et al. (Aug. 21, 2018). "Non-Viral Delivery of Nucleic Acids: Insight into Mechanisms of Overcoming Intracellular Barriers," Front Pharmacol. 9(971):1-15.

Enuka, Y. et al. (2016, e-pub. Dec. 10, 2015). "Circular RNAs Are Long-Lived and Display Only Minimal Early Alterations In Response To a Growth Factor," Nucleic Acids Res. 44(3):1370-1383.

Fenton, O.S. et al. (Apr. 20, 2016). "Bioinspired Alkenyl Amino Alcohol Ionizable Lipid Materials for Highly Potent In Vivo mRNA Delivery," Adv. Mater. 28(15):2939-2943, 11 pages.

Fischer, J. W. et al. (Apr. 2017). "CircRNAs: A Regulator of Cellular Stress," Crit. Rev. Biochem. Mol. Biol. 52 (2):220-233, 27 pages.

Focosi, D. et al. (2021). "Neutralising Antibody Escape of SARS-CoV-2 Spike Protein: Risk Assessment for Antibody-Based Covid-19 Therapeutics and Vaccines," Rev. Med. Virol. 31:e2231, 21 pages.

Ford, E. et al. (Apr. 1994). "Synthesis of Circular RNA in bacteria and Yeast Using RNA Cyclase Ribozymes Derived from a Group I Intron of Phage T4," Proc. Natl Acad. Sci. 91:3117-3121.

Gao, Q. et al. (Jul. 3, 2020, e-pub. May 6, 2020). "Development of an Inactivated Vaccine Candidate For SARS-CoV-2," Science 369(6499):77-81, 5 pages.

Gao, X. et al. (Mar. 2021). "Circular RNA-Encoded Oncogenic E-Cadherin Variant Promotes Glioblastoma Tumorigenicity Through Activation of EGFR-STAT3 Signalling," Nat. Cell Biol. 23:278-291.

Garcia-Beltran, W.F. et al. (Apr. 29, 2021). "Multiple SARS-CoV-2 Variants Escape Neutralization by Vaccine-Induced Humoral Immunity," Cell 184:2372-2383.

(56)　　　　References Cited

OTHER PUBLICATIONS

Gu, H. et al. (Sep. 25, 2020). "Adaptation of SARS-CoV-2 in BALB/c Mice for Testing Vaccine Efficacy," Science 369:1603-1607.

Gupta, R.K. (Jun. 2021). "Will SARS-CoV-2 Variants of Concern Affect the Promise of Vaccines?" Nat. Rev. Immunol. 21:340-341.

Hacisuleyman, E. et al. (Apr. 21, 2021). "Vaccine Breakthrough Infections with SARS-CoV-2 Variants," N. Engl. J. Med., 7 pages.

He, X. et al. (2020, e-pub. May 28, 2020). "Immune Checkpoint Signaling and Cancer Immunotherapy," Cell Res. 30:660-669.

Hoffmann, M. et al. (Apr. 16, 2020). "SARS-CoV-2 Cell Entry Depends on ACE2 and TMPRSS2 and Is Blocked by a Clinically Proven Protease Inhibitor," Cell 181(2):271-280, 20 pages.

Hoffmann, M. et al. (Apr. 29, 2021). "SARS-CoV-2 Variants B.1.351 and P.1 Escape from Neutralizing Antibodies," Cell 184:2384-2393.

Hsieh, C. L. et al. (2020, e-pub. Jul. 23, 2020). "Structure-Based Design of Prefusion-Stabilized SARS-CoV-2 Spikes," Science 369:1501-1505, 9 pages.

Huang, Q. et al. (2021). "A Single-Dose mRNA Vaccine Provides a Long-Term Protection for hACE2 Transgenic Mice From SARS-CoV-2," Nat. Commun. 12: 776, 10 pages.

International Preliminary Report on Patentability, issued Feb. 16, 2023, for PCT Application No. PCT/CN2021/113865, filed Aug. 20, 2021, 8 pages.

International Preliminary Report on Patentability, issued Feb. 27, 2024, for PCT Application No. PCT/CN2022/082225, filed Mar. 22, 2022, 4 pages.

International Preliminary Report on Patentability, issued Jul. 30, 2024, for PCT Application No. PCT/CN2023/073619, Jan. 28, 2023, 6 pages.

International Preliminary Report on Patentability, issued Jun. 20, 2024, for PCT Application No. PCT/CN2022/071347, Jan. 11, 2022, 7 pages.

International Preliminary Report on Patentability, issued Jun. 20, 2024, for PCT Application No. PCT/CN2022/082224, filed Mar. 22, 2022, 6 pages.

International Preliminary Report on Patentability, issued Jun. 20, 2024, for PCT Application No. PCT/CN2023/071196, filed Jan. 9, 2023, 6 pages.

International Search Report and Written Opinion, mailed Mar. 31, 2023, for PCT Application No. PCT/CN2023/071196, filed Jan. 9, 2023, 13 pages.

Jackson, N.A.C. et al. (2020). "The Promise of mRNA Vaccines: A Biotech and Industrial Perspective," NPJ Vaccines 5:11, 6 pages.

Kim, D. et al. (May 14, 2020). "The Architecture of SARS-CoV-2 Transcriptome," Cell 181:914-921.

Koenig, P.A. et al. (Feb. 12, 2021). "Structure-Guided Multivalent Nanobodies Block SARS-CoV-2 Infection and Suppress Mutational Escape," Science 371:eabe6230, 16 pages.

Kou, Y. et al. (2017, e-pub. Jul. 17, 2017). "Tissue Plasminogen Activator (tPA) Signal Sequence Enhances Immunogenicity of MVA-Based Vaccine Against Tuberculosis," Immunol. Lett. 190:51-57.

Krammer, F. (Oct. 22, 2020, e-pub. Sep. 23, 2020). "SARS-CoV-2 Vaccines in Development," Nature 586:516-527.

Kristensen, L.S. et al. (Nov. 2019, e-pub. Aug. 8, 2019). "The Biogenesis, Biology and Characterization of Circular RNAs," Nat. Rev. Genet. 20:675-691.

Laczkó, D. et al. (Oct. 13, 2020). "A Single Immunization with Nucleoside-Modified mRNA Vaccines Elicits Strong Cellular and Humoral Immune Responses Against SARS-CoV-2 in Mice," Immunity 53:724-732.

Lauring, A. S. et al. (Feb. 9, 2021). "Genetic Variants of SARS-CoV-2—What Do They Mean?" JAMA 325(6):529-531.

Legnini, I. et al. (Apr. 6, 2017). "Circ-ZNF609 Is a Circular RNA that Can Be Translated and Functions in Myogenesis," Mol Cell 66:22-37.

Li, Q. et al. (Apr. 29, 2021). "SARS-CoV-2 501Y.V2 Variants Lack Higher Infectivity but do Have Immune Escape," Cell 184:2362-2371.

Linsky, T.W. et al. (Dec. 4, 2020). "De Novo Design of Potent and Resilient hACE2 Decoys to Neutralize SARS-CoV-2," Science 370:1208-1214.

Madhi, S.A. et al. (Mar. 16, 2021). "Efficacy of the ChAdOx1 nCoV-19 Covid-19 Vaccine Against the B.1.351 Variant," N. Engl. J. Med., 14 pages.

Memczak, S. et al. (Mar. 21, 2013, e-pub. Feb. 27, 2013). "Circular RNAs Are a Large Class of Animal RNAs With Regulatory Potency," Nature 495(7441):333-338, 10 pages.

Montagutelli, X. et al. (2021). "The B1.351 and P. 1 Variants Extend SARS-CoV-2 Host Range to Mice," bioRxiv, 16 pages.

Muik, A. et al. (Mar. 12, 2021). "Neutralization of SARS-CoV-2 Lineage B.1.1.7 Pseudovirus by BNT162b2 Vaccine-Elicited Human Sera," Science 371:1152-1153.

Mukhopadhyay, S. et al. (Mar. 2021). "The Metabolic Landscape of RAS-Driven Cancers from Biology to Therapy," Nat. Cancer 2(3):271-283, 29 pages.

Mullard, A. (Jun. 6, 2020). "COVID-19 Vaccine Development Pipeline Gears Up," Lancet 395:1751-1752.

Ou, X. et al. (2020). "Characterization of Spike Glycoprotein of SARS-CoV-2 on Virus Entry and its Immune Cross-Reactivity with SARS-CoV," Nat. Commun. 11:1620, 12 pages.

Papanikolopoulou, K. et al. (2008). "Creation of Hybrid Nanorods from Sequences of Natural Trimeric Fibrous Proteins Using the Fibritin Trimerization Motif," in Methods Mol. Biol. 474:15-33, 270 pages.

Pardi, N. et al. (Apr. 2018). "mRNA Vaccines—A New Era in Vaccinology," Nat. Rev. Drug Discov. 17(4):261-279, 43 pages.

Pardi, N. et al. (Mar. 9, 2017). "Zika Virus Protection by a Single Low-Dose Nucleoside-Modified mRNA Vaccination," Nature 543(7644):248-251, 21 pages.

Pinto, D. et al. (Jul. 9, 2020, e-pub. May 18, 2020). "Cross-Neutralization of SARS-CoV-2 by a Human Monoclonal SARS-CoV Antibody," Nature 583:290-295, 22 pages.

Planas, D. et al. (May 2021). "Sensitivity of Infectious SARS-CoV-2 B.1.1.7 and B.1.351 Variants to Neutralizing Antibodies," Nat. Med. 27:917-924.

Puttaraju, M. et al. (1992). "Group I Permuted Intron-Exon (PIE) Sequences Self-Splice To Produce Circular Exons," Nucleic Acids Res. 20(20):5357-5364.

Richner, J.M. et al. (Mar. 9, 2017). "Modified mRNA Vaccines Protect Against Zika Virus Infection," Cell 168:1114-1125, 1 page.

Sabapathy, K. et al. (Jan. 2018, e-pub. Sep. 26, 2017). "Therapeutic Targeting of p53: All Mutants are Equal, but Some Mutants are More Equal Than Others," Nat. Rev. Clin. Oncol. 15:13-30.

Sahin, U. et al. (Oct. 22, 2020, e-pub. Sep. 30, 2020). "COVID-19 Vaccine BNT162b1 Elicits Human Antibody and TH1T Cell Responses," Nature 586:594-599, 23 pages.

Sanchez-Felipe, L. et al. (Feb. 11, 2021, e-pub. Dec. 1, 2020). "A Single-Dose Live-Attenuated YF17D-Vectored SARS-CoV-2 Vaccine Candidate," Nature 590:320-325, 24 pages.

Schoof, M. et al. (Dec. 18, 2020). "An Ultrapotent Synthetic Nanobody Neutralizes SARS-CoV-2 by Stabilizing Inactive Spike," Science 370:1473-1479.

Sette, A. et al. (Feb. 18, 2021). "Adaptive Immunity to SARS-CoV-2 and COVID-19," Cell 184:861-880.

Shang, J. et al. (May 26, 2020, e-pub. May 6, 2020). "Cell Entry Mechanisms of SARS-CoV-2," Proc. Natl. Acad. Sci. USA 117:11727-11734.

Tai, W. et al. (2020, e-pub. Aug. 2020). "A Novel Receptor-Binding Domain (RBD)-Based mRNA Vaccine Against SARS-CoV-2," Cell Res. 30:932-935.

Tan, C.W. et al. (Sep. 2020). "A SARS-CoV-2 Surrogate Virus Neutralization Test Based on Antibody-Mediated Blockage of ACE2-Spike Protein-Protein Interaction," Nat. Biotechnol. 38:1073-1078, 17 pages.

V'kovski, P. et al. (Mar. 2021). "Coronavirus Biology and Replication: Implications for SARS-CoV-2," Nat. Rev. Microbiol. 19:155-170.

(56)                    References Cited

OTHER PUBLICATIONS

Van Doremalen, N. et al. (Oct. 2020). "ChAdOx1 nCoV-19 Vaccine Prevents SARS-CoV-2 Pneumonia in Rhesus Macaques," Nature 586(7830):578-582, 21 pages.

Vicens, Q. et al. (2008). "Toward Predicting Self-Splicing and Protein-Facilitated Splicing of Group I Introns," RNA 14:2013-2029.

Vogel, A.B. et al. (Apr. 8, 2021, e-pub. Feb. 1, 2021). "BNT162b Vaccines Protect Rhesus Macaques from SARS-CoV-2," Nature 592:283-289, 35 pages.

Walls, A. C. et al. (Apr. 16, 2020). "Structure, Function, and Antigenicity of the SARS-CoV-2 Spike Glycoprotein," Cell 180(2):281-292, 38 pages.

Wang, G. L. et al. (2021). "Susceptibility of Circulating SARS-CoV-2 Variants to Neutralization," N. Engl. J. Med., 3 pages.

Wang, P. et al. (May 6, 2021, e-pub. Mar. 8, 2021). "Antibody Resistance of SARS-CoV-2 Variants B.1.351 and B.1.1.7," Nature 593:130-135, 18 pages.

Wang, Z. et al. (Apr. 2021). "mRNA Vaccine-Elicited Antibodies to SARS-CoV-2 and Circulating Variants," Nature 592(7855):616-622, 30 pages.

Wibmer, C.K. et al. (Apr. 2021). "SARS-CoV-2 501Y.V2 Escapes Neutralization by South African COVID-19 Donor Plasma," Nat. Med. 27:622-625.

Wrapp, D. et al. (Mar. 13, 2020, e-pub. Feb. 19, s2020). "Cryo-EM Structure of the 2019-nCoV Spiked in the Prefusion Conformation," Science 367:1260-1263.

Wu, F. et al. (Mar. 12, 2020, e-pub. Feb. 3, 2020). "A New Coronavirus Associated with Human Respiratory Disease in China," Nature 579:265-269, 20 pages.

Xiang, Y. et al. (Dec. 18, 2020). "Versatile and Multivalent Nanobodies Efficiently Neutralize SARS-CoV-2," Science 370:1479-1484.

Yan, R. et al. (Mar. 27, 2020). "Structural Basis for the Recognition of SARS-CoV-2 by Full-Length Human ACE2," Science 367:1444-1448.

Yang, J. et al. (Oct. 22, 2020, e-pub. Jul. 29, 2020). "A Vaccine Targeting the RBD of the S Protein of SARS-CoV-2 Induces Protective Immunity," Nature 586:572-577, 21 pages.

Yang, Y. et al. (2017, e-pub. Mar. 10, 2017). "Extensive Translation of Circular RNAs Driven by N6-Methyladenosine," Cell Res 27:626-641.

Yu, J. et al. (Aug. 14, 2020). "DNA Vaccine Protection Against SARS-CoV-2 in Rhesus Macaques," Science 369:806-811.

Zhang, M. et al. (2018). "A Peptide Encoded by Circular Form of LINC-PINT Suppresses Oncogenic Transcriptional Elongation in Glioblastoma," Nat. Commun. 9:4475, 17 pages.

Zhang, N. N. et al. (Sep. 3, 2020). "A Thermostable mRNA Vaccine Against COVID-19," Cell 182:1271-1283, 30 pages.

Zhang, X.O. et al. (Sep. 25, 2014). "Complementary Sequence-Mediated Exon Circularization," Cell 159:134-147.

Zhou, P. et al. (Mar. 12, 2020, e-pub. Feb. 3, 2020). "A Pneumonia Outbreak Associated With a New Coronavirus of Probable Bat Origin," Nature 579:270-273, 20 pages.

Zhu, F.C. et al. (Jun. 13, 2020, e-pub. May 22, 2020). "Safety, Tolerability, and Immunogenicity of a Recombinant Adenovirus Type-5 Vectored COVID-19 vaccine: A Dose-Escalation, Open-Label, Non-Randomised, First-In-Human Trial," Lancet 395:1845-1854.

Altschul, S.F. et al. (1990). "Basic Local Alignment Search Tool," J. Mol. Biol. 215:403-410, 11 pages.

Amanat, F. et al. (Apr. 14, 2020). "SARS-CoV-2 Vaccines: Status Report," Immunity 52:583-589.

Baird, S.D. et al. (Oct. 2006). "Searching for IRES," RNA 12(10):1755-1785.

Barnes, C.O. et al. (Dec. 24-31, 2020, e-pub. Oct. 12, 2020). "SARS-CoV-2 Neutralizing Antibody Structures Inform Therapeutic Strategies," Nature 588:682-687, 22 pages.

Bringmann, A. et al. (2010). "RNA Vaccines in Cancer Treatment," Journal of Biomedicine and Biotechnology 2010 (623687):1-13.

Carrillo, H. et al. (Oct. 1988). "The Multiple Sequence Alignment Problem in Biology," SIAM J Applied Math 48 (5):1073-1082.

Chen, C.Y. et al. (Apr. 21, 1995). "Initiation of Protein Synthesis by the Eukaryotic Translational Apparatus on Circular RNAs," Science 268:415-417.

Chen, X. et al. (Oct. 15, 2013). "Fusion Protein Linkers: Property, Design and Functionality," Adv. Drug Deli Rev. 65(10):1357-1369, 32 pages.

ClinicalTrials.gov (Apr. 6, 2020). NCT04335136—Recombinant Human Angiotensin-converting Enzyme 2 (rhACE2) as a Treatment for Patients With COVID-19 (APN01-COVID-19), 9 pages.

Devereux, J. et al. (1984). "A Comprehensive Set Of Sequence Analysis Programs For The VAX," Nucleic Acids Research 12(1):387-395.

Edgar, R.C. (2004, e-pub. Mar. 19, 2004). "MUSCLE: Multiple Sequence Alignment With High Accuracy and High Throughput," Nucleic Acids Research 32(5):1792-1797.

Edgar, R.C. (Aug. 19, 2004). "MUSCLE: A Multiple Sequence Alignment Method With Reduced Time and Space Complexity," bmc Bioinformatics 5:113, pp. 1-19.

Forster, P. et al. (Apr. 28, 2020). "Phylogenetic Network Analysis of SARS-CoV-2 Genomes," PNAS 117 (17):9241-9243.

Genbank Accession Number (Jul. 21, 2004). "AAT74874—Spike Protein [SARS Coronavirus HHS-2004]," 3 pages.

Glasgow, A. et al. (Nov. 10, 2020). "Engineered ACE2 Receptor Traps Potently Neutralize SARS-CoV-2," PNAS 117(45):28046-28055.

Haschke, M. et al. (Sep. 2013, e-pub. May 17, 2013). "Pharmacokinetics and Pharmacodynamics of Recombinant Human Angiotensin-Converting Enzyme 2 in Healthy Human Subjects," Clin. Pharmacokinet. 52 (9):783-792.

Higuchi, Y. et al. (Dec. 14, 2020). "High Affinity Modified ACE2 Receptors Protect from SARSSARS-CoV-2 Infection in Hamsters," bioRxiv, 37 pages.

Hofacker, I.L. (2003). "Vienna RNA Secondary Structure Server," Nucleic Acids Res. 31(13):3429-3431.

Ickenstein, L.M. et al. (Nov. 2019, Sep. 17, 2019). "Lipid-Based Nanoparticle Formulations for Small Molecules and RNA Drugs," Expert Opin. Drug Deliv., 77 pages.

International Search Report and Written Opinion, mailed Jun. 27, 2022, for PCT Application No. PCT/CN2022/082225, filed Mar. 22, 2022, 11 pages.

International Search Report and Written Opinion, mailed May 17, 2023, for PCT Application No. PCT/CN2023/073619, Jan. 28, 2023, 14 pages.

International Search Report and Written Opinion, mailed Nov. 25, 2021, for PCT Application No. PCT/CN2021/113865, filed Aug. 20, 2021, 14 pages.

International Search Report and Written Opinion, mailed Oct. 12, 2022, for PCT Application No. PCT/CN2022/071347, Jan. 11, 2022, 15 pages.

International Search Report and Written Opinion, mailed Sep. 27, 2022, for PCT Application No. PCT/CN2022/082224, filed Mar. 22, 2022, 11 pages.

Ke, S. et al. (2017). "m6A mRNA Modifications are Deposited in Nascent Pre-mRNA and are Not Required for Splicing but do Specify Cytoplasmic Turnover," Genes & Dev. 31:990-1006.

Meyers, E. et al. (1988). "Optimal Alignments in Linear Space," Comput. Appl. Biosci., 4(1):11-17.

NCBI Reference (Aug. 8, 2020). "YP 009047204.1—Spike Protein [Middle East Respiratory Syndrome-Related Coronavirus]," 3 pages.

NCBI Reference (Jul. 18, 2020). YP 009724390—Surface Glycoprotein [Severe Acute Respiratory Syndrome Coronavirus 2], 3 pages.

Petkovic, S. et al. (Feb. 27, 2015, e-pub. Feb. 6, 2015). "RNA Circularization Strategies in vivo and in vitro," Nucleic Acids Res. 43(4):2454-2465.

Qu, L. et al. (Mar. 16, 2021). "Circular RNA Vaccines Against SARS-CoV-2 and Emerging Variants," bioRxiv 56 pages.

Qu, L. et al. (Sep. 30, 2019, e-pub. Jul. 15, 2019). "Programmable RNA Editing By Recruiting Endogenous ADAR Using Engineered RNAs," Nature Biotechnology 37:1059-1069, 16 pages.

Remington'S Pharmaceutical Sciences. (1980). 16th edition, Osol, A. Ed, pp. 1-2, (Table of Contents Only).

(56)          References Cited

OTHER PUBLICATIONS

Semple, S.C. et al. (Feb. 2010, e-pub. Jan. 17, 2010). "Rational Design Of Cationic Lipids For siRNA Delivery," Nat. Biotechnol. 28(2):172-176.

Sliepen, K. et al. (Mar. 20, 2015). "Immunosilencing a Highly Immunogenic Protein Trimerization Domain," The Journal of Biol. Chem. 290(12):7436-7442.

Vazquez-Lombardi, R. et al. (Oct. 2015). "Challenges and Opportunities for Non-Antibody Scaffold Drugs," Drug Discovery Today 20(10):1271-1283.

Vigneron, N. et al. (Jul. 15, 2013). "Database of T Cell-Defined Human Tumor Antigens: The 2013 Update," Cancer Immunity 13(15):1-6.

Wesselhoeft, R.A. et al. (2018, e-pub. Jul. 6, 2018). "Engineering Circular RNA For Potent and Stable Translation In Eukaryotic Cells," Nat. Commun. 9:2629, 10 pages.

Wesselhoeft, R.A. et al. (2019, e-pub. May 2, 2019). "RNA Circularization Diminishes Immunogenicity and Can Extend Translation Duration In Vivo," Mol. Cell 74(3):508-520, 18 pages.

Yang, X. et al. (2009, e-pub. Dec. 19, 2008). "An Introduction to Epitope Prediction Methods and Software" Rev. Med. Virol. 19(2):77-96.

Zhang, M.L. et al. (Mar. 31, 2018, e-pub. Jan. 18, 2018). "A Novel Protein Encoded By the Circular Form of the SHPRH Gene Suppresses Glioma Tumorigenesis," Oncogene 37(13):1805-1814, 10 pages.

Zuker, M. (2003). "Mfold Web Server For Nucleic Acid Folding and Hybridization Prediction," Nucleic Acids Res. 31(13):3406-3415.

Chen, H. et al. (2020, e-pub. Mar. 30, 2020). "Preferential Production of RNA Rings T4 RNA Ligase 2 Without Any Splint Through Rational Design of Precursor Strand," Nucleic Acids Research 48(9):e54, 12 pages.

Cheng, K. et al. (Jan. 1, 2019). "RNA Ligation of Very Small Pseudo Nick Structures by T4 RNA Ligase 2, Leading to Efficient Production of Versatile RNA Rings," RSC Advances 9(15):8620-8627.

Sean, P. et al. (2009, e-pub. May 14, 2009). "Altered Interactions Between Stem-Loop IV Withing the 5' Noncoding Region of Coxsackievirus RNA and Poly(rC) Binding Protein 2: Effects on IRES-Mediated Translation and Viral Infectivity," Virology 389(1-2):45-58.

Maloney, A. et al. (Jan. 2, 2024, e-pub. Dec. 11, 2023). "Validating the EMCV IRES Secondary Structure with Structure-Function Analysis," Biochemistry 63(1):107-115, 18 pages.

Costello, A. et al. (2019) "Continuous Translation of Circularized mRNA Improves Recombinant Protein Titer," Metabolic Engineering 52:284-292.

* cited by examiner

CVB3 IRES

Site1

Site2

Original

Site1

Site2

FIG. 4B          FIG. 5A

Any RNA sequence

Split RNA element

Split site potential split site sgRNA

Split site

CONSTRUCTS AND METHODS FOR PREPARING CIRCULAR RNA

CROSS REFERENCE TO RELATED APPLICATIONS

This application is a continuation application of International Application No. PCT/CN2022/082225, filed internationally on Mar. 22, 2022, which claims priority benefit from International Patent Application No. PCT/CN2021/115029, filed on Aug. 27, 2021, the contents of each of which are incorporated herein by reference in their entireties.

REFERENCE TO AN ELECTRONIC SEQUENCE LISTING

The contents of the electronic sequence listing (165392000701SEQLIST.xml; Size: 25,804 bytes; and Date of Creation: Feb. 26, 2025) is herein incorporated by reference in its entirety.

FIELD

The present application relates to constructs and methods for preparing circular RNA (circRNA) comprising an effector RNA (e.g., coding RNA) sequence, circRNAs prepared thereof, and methods of use thereof.

BACKGROUND

In recent years, circular RNAs (circRNAs) with coding ability have been discovered, but there are still challenging in producing circular RNAs with coding ability accurately and efficiently in vitro. Current methods for generating circular RNAs mainly fall into two categories according to the enzyme used. The first category of methods leverage autocatalysis of a Group I intron to produce circular RNAs. The second category of methods use a T4 RNA ligase to produce circular RNAs. T4 RNA ligase 1-mediated ligation is a commonly used method for cyclizing RNA, but it does not accurately ligate the ends of a linear RNA due to insertions and deletions introduced during the ligation process. Furthermore, splint oligonucleotide is often required to bring the two ends of a linear RNA precursor together in order to allow efficient ligation of the linear RNA precursor into a circular RNA. The splint oligonucleotide has to be removed after ligation, and polymeric by-products may form.

There is need for methods of preparing circRNAs at high yields and without use of a splint oligonucleotide or introducing unnecessary sequences at the ends of a coding RNA.

BRIEF SUMMARY

The present application provides linear RNAs and constructs for preparing circRNAs by ligation, and methods for preparing circRNAs.

One aspect of the present application provides a linear RNA, comprising from the 5' end to the 3' end: (a) a first portion of a RNA element; (b) an effector RNA sequence; and (c) a second portion of the RNA element; wherein the first portion of the RNA element and the second portion of the RNA element associate with each other to form a double-stranded region of at least 4 basepairs (bp) long; wherein the 5' end of the first portion of the RNA element and the 3' end of the second portion of the RNA element form a nick in the double-stranded region; and wherein the nick can be ligated by a RNA ligase (e.g., T4 RNA ligase 1 or T4 RNA ligase 2). In some embodiments, the double-stranded region is at least 6 bp, 8 bp, 10 bp, 12 bp, or more bp long. In some embodiments, the double-stranded region is about 6 bp long to about 25 bp long. In some embodiments, the double-stranded region has a minimum free energy of no more than about $-8$ kcal/mol (e.g., no more than $-9$, $-10$, $-11$, $-12$, $-13$, $-14$, $-15$, $-16$ kcal/mol or lower) at 37° C. and an ionic strength of 1.0M Na$^+$, e.g., as predicted by RNAfold or Mfold.

In some embodiments according to any one of the linear RNAs described above, the RNA element is at least about 20 nt long, such as at least about 50, 100, 200, 300, 500, 600, 700, 800, 900, 1000 or more nt long.

In some embodiments according to any one of the linear RNAs described above, the double-stranded region comprises at least 2 bp 3' to the nick. In some embodiments, the double-stranded region comprises about any one of 2, 3, 4, 5, 6 or more basepairs 3' to the nick.

In some embodiments according to any one of the linear RNAs described above, the double-stranded region comprises at least 2 (e.g., at least 4) bp 5' to the nick. In some embodiments, the double-stranded region comprises about any one of 2, 3, 4, 5, 6, 7, 8, 9, 10, 11, 12, or more basepairs 5' to the nick.

In some embodiments according to any one of the linear RNAs described above, the first portion of the RNA element and the second portion of the RNA element are derived from a reference RNA element of N nucleotides, wherein N is an integer greater than 8; wherein the first portion of the RNA element comprises nucleotides X to N of the reference RNA element, wherein X is an integer greater than 1 and smaller than N; and wherein the second portion of the RNA element comprises nucleotides 1 to X-1 of the reference RNA element. In some embodiments, the first portion of the RNA element and/or the second portion of the RNA element comprises a sequence that is exogenous to the reference RNA element. In some embodiments, the second portion of the RNA element comprises a first exogenous sequence at the 3' end, wherein the first portion of the RNA element comprises a second exogenous sequence that is complementary of the first exogenous sequence, and wherein the first exogenous sequence and the second exogenous sequence form basepairs flanking the 5' end of the nick. In some embodiments, the first exogenous sequence and/or the second exogenous sequence is at least 4 nt long. In some embodiments, the first exogenous sequence is GUUU.

In some embodiments according to any one of the linear RNAs described above, the RNA element is a naturally occurring RNA element or a derivative thereof. In some embodiments, the RNA element is a sgRNA. In some embodiments, the RNA element is an H/ACA box snoRNA.

In some embodiments according to any one of the linear RNAs described above, the effector RNA sequence is a coding RNA sequence. In some embodiments, the coding RNA sequence encodes a therapeutic polypeptide. In some embodiments, the therapeutic polypeptide is selected from the group consisting of an antigenic polypeptide (e.g., an antigenic polypeptide of a pathogen, or a tumor antigen peptide), a functional protein (e.g., an enzyme), a receptor protein (e.g., a soluble receptor), and a targeting protein (e.g., an antibody or antigen-binding fragment thereof).

In some embodiments according to any one of the linear RNAs described above, wherein the effector RNA sequence is a coding RNA sequence, the RNA element promotes translation of the coding RNA sequence. In some embodiments, the RNA element is an internal ribosomal entry site (IRES) or a portion thereof. In some embodiments, the IRES is derived from an IRES selected from the group consisting of Coxsackievirus B3 (CVB3) IRES, Enterovirus 71 (EV71) IRES, encephalomyocarditis virus (EMCV) IRES, picornavirus (PV) IRES, hepatitis C virus (HCV) IRES, adenovirus (AdV) IRES, human papillomavirus type 31 (HPV31) IRES, human herpesvirus (HHV) IRES, Rous sarcoma virus (RSV) IRES, classical swine fever virus (CSFV) IRES, FGF9 IRES, SLC7A1 IRES, and RUNX1 IRES. In some embodiments, the IRES is an IRES of a CVB3 virus or a derivative thereof. In some embodiments, the IRES of a CVB3 virus comprises the nucleotide sequence of SEQ ID NO: 1. In some embodiments, the first portion of the RNA element comprises nucleotides 382-741 of SEQ ID NO: 1, and wherein the second portion of the RNA element comprises nucleotides 1-381 of SEQ ID NO: 1. In some embodiments, the first portion of the RNA element comprises the nucleotide sequence of SEQ ID NO: 3, and wherein the second portion of the RNA element comprises the nucleotide sequence of SEQ ID NO: 2. In some embodiments, the first portion of the RNA element comprises nucleotides 343-741 of SEQ ID NO: 1, and wherein the second portion of the RNA element comprises nucleotides 1-342 of SEQ ID NO: 1.

In some embodiments according to any one of the linear RNAs described above, wherein the effector RNA sequence is a coding RNA sequence, the linear RNA further comprising an in-frame 2A peptide (e.g., T2A or P2A) coding sequence that is operably linked to the 3' end of the coding RNA.

In some embodiments according to any one of the linear RNAs described above, the effector RNA sequence is a sequence of a non-coding RNA selected from the group consisting of a guide RNA (gRNA), a deaminase-recruiting RNA (dRNA), a short interfering RNA (siRNA), a microRNA (miRNA), a short hairpin RNA (shRNA), and a long intervening non-coding (line) RNA.

In some embodiments according to any one of the linear RNAs described above, the effector RNA sequence is at least about 50 nucleotides (nt) long, such as at least about any one of 60, 90, 120, 150, 200, 300, 400, 500, 600, 800, 1000, 1200, 1500 or more nt long. In some embodiments, the effector RNA sequence is about 50 nt to about 5000 nt long.

In some embodiments, there is provided a nucleic acid construct comprising a nucleic acid sequence encoding the linear RNA according to any one of the linear RNAs described above. In some embodiments, the nucleic acid construct comprises a T7 promoter operably linked to the nucleic acid sequence encoding the linear RNA.

Another aspect of the present application provides a method of preparing a circRNA, comprising: (a) contacting the linear RNA according to any one of the linear RNAs described above with a RNA ligase under conditions that allow ligation of the nick in the linear RNA to provide a circularized RNA product; and (b) isolating the circularized RNA product, thereby providing the circRNA. In some embodiments, the T4 RNA ligase is T4 RNA ligase 1. In some embodiments, the T4 RNA ligase is T4 RNA ligase 2. In some embodiments, the circRNA does not comprise nucleotide sequence that is exogenous to the linear RNA, such as insertion or deletion introduced by ligation. In some embodiments, the ligation does not require presence of a splint oligonucleotide. In some embodiments, efficiency of the ligation is at least about 50% (e.g., at least about 60`, 65%, 70%, 75%, 80%, 85%, 90% or higher).

In some embodiments according to any one of the methods of preparation described above, the method further comprises treating the circularized RNA product with RNAse R. In some embodiments, the method further comprises purifying the circularized RNA product. In some embodiments, the method further comprises obtaining the linear RNA by in vitro transcription of a nucleic acid construct comprising a nucleic acid sequence encoding the linear RNA.

Also provided is a circRNA prepared using the method according to any one of the methods of preparation described above.

In some embodiments, there is provided a circRNA formed by ligation of the nick in the linear RNA according to any one of the linear RNAs described above. In some embodiments, the circRNA is a circRNA vaccine.

In some embodiments, there is provided a method of treating or preventing a disease or condition in a subject in need thereof, comprising administering to the subject an effective account of any one of the circRNAs described above.

Further provided are compositions, kits and articles of manufacture for use in any one of the methods described above.

BRIEF DESCRIPTION OF THE DRAWINGS

FIG. 4B shows Western blot results detecting EGFP expression in cells after 24 hours of transfection with Site1 ligation circular RNA.

FIG. 5A shows PCR amplified products across the ligation junction using precursor RNA transcript and Site 1 ligation circular RNA samples.

DETAILED DESCRIPTION

Figure 1:
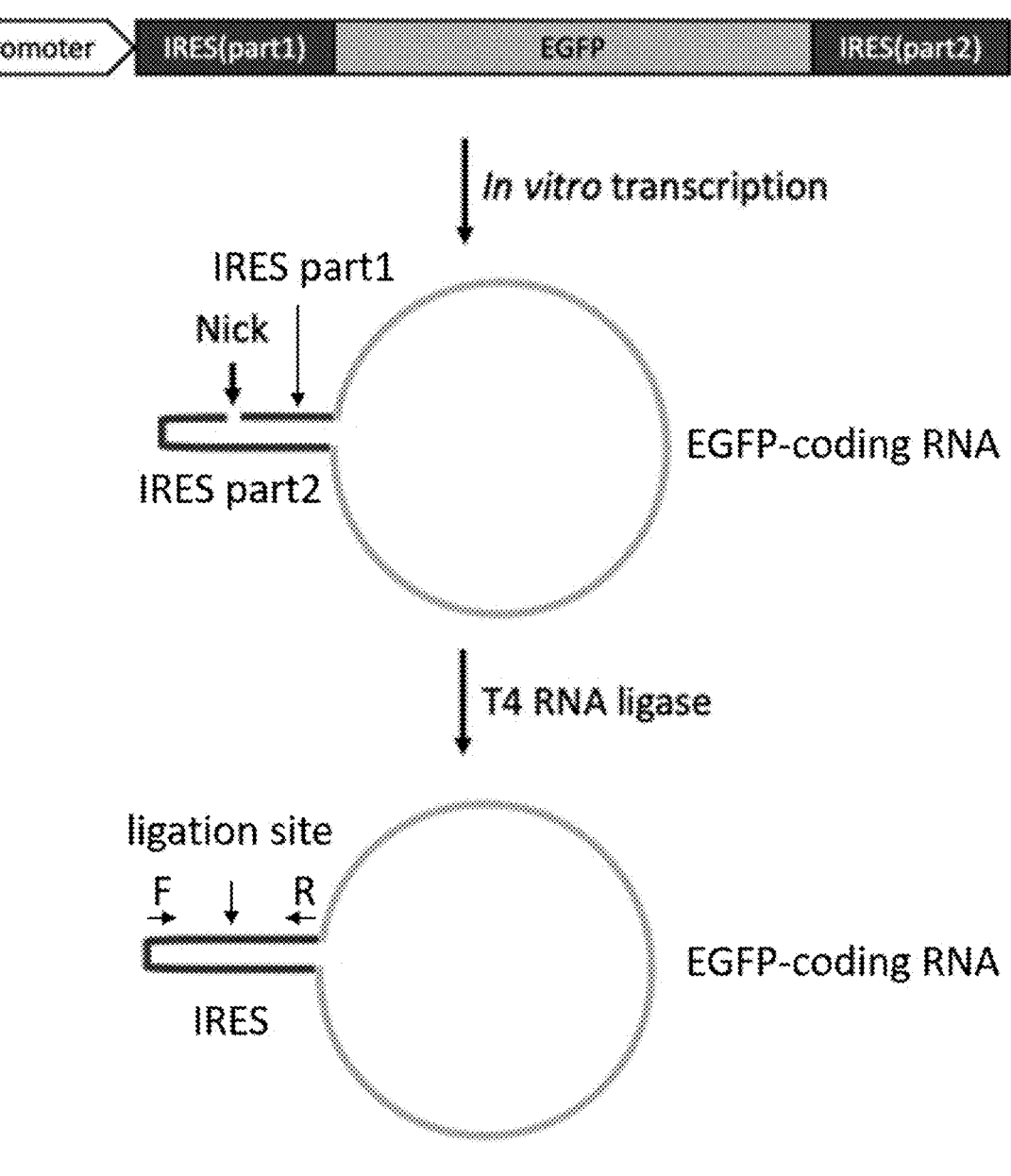
FIG. 1 is a schematic showing production of a coding circular RNA using a T4 RNA ligase that ligates two portions of an IRES element in a linear RNA construct. The EGFP-coding RNA is the arch portion of the RNA transcript after in vitro transcription and ligation by a T4 RNA ligase. The nick in the linear RNA construct corresponds to the ligation site in the circular RNA product. Forward (F) and reverse (R) primers surrounding the ligation site were designed to detect ligation by reverse transcription followed by PCR amplification of a sequence encompassing the ligation site.

The present application provides linear RNA precursors and constructs for preparing circular RNAs (circRNAs) comprising an effector RNA (e.g., coding RNA) sequence. The linear RNA precursors described herein comprise from the 5' end to the 3' end: a first split portion of an RNA element, an effector RNA (e.g., coding RNA) sequence, and a second split portion of the RNA element, wherein the RNA element has a stable double-stranded region. The two split portions in the linear RNA precursor can associate with each other to reconstitute the RNA element, and form a nick in the stable double-stranded region. Ligation of the nick using an RNA ligase (such as T4 RNA ligase 1 or T4 RNA ligase 2) gives rise to a circRNA. In some embodiments, the RNA element is an internal ribosomal entry site (IRES), such as an IRES of a CVB3 virus. Also provided are methods of preparing circRNAs using the linear RNA precursors and constructs described herein. The methods allow in vitro production of circRNAs at high efficiency, accuracy, and without use of a splint oligonucleotide. Furthermore, split portions of the RNA elements used to promote intramolecular ligation in the methods described herein may serve functional roles, e.g., promoting translation of a coding RNA sequence, thereby avoiding introducing additional ligation sequences that may have immunogenicity or reduce cargo size of the circRNA.

Accordingly, in some embodiments, there is provided a linear RNA comprising from the 5' end to the 3' end: (a) a first portion of an RNA element (such as an IRES), (b) an effector RNA (e.g., coding RNA) sequence, and (c) a second portion of the RNA element, wherein the first portion of the RNA element and the second portion of the RNA element associate with each other to form a double-stranded region of at least 4 basepairs (bp) long, wherein the 5' end of the first portion of the RNA element and the 3' end of the second portion of the RNA element form a nick in the double-stranded region, and wherein the nick can be ligated by a RNA ligase (e.g., T4 RNA ligase 2).

I. Definitions

Terms are used herein as generally used in the art, unless otherwise defined as follows.

The term "linear RNA" refers to a RNA molecule having a 5' end and a 3' end. A linear RNA may have secondary structures, including helices and loop regions.

The term "RNA element" refers to a RNA motif that folds into secondary structures, including double-stranded regions. In some embodiments, the RNA element is a cis-regulatory RNA element that regulates nucleic acid regions on the same molecule. The RNA element may be a naturally occurring RNA element (e.g., IRES), or a man-made RNA element (e.g., an aptamer).

The term "first portion" and "second portion" of an RNA element are used interchangeably herein with "'5' portion" and "3' portion", "first split portion" and "second split portion", or "first split" and "second split" of an RNA element to refer to engineered segments of a reference RNA element that can self-assemble into substantially the same secondary structures as the RNA element. In some embodiments, a reference RNA element can be divided or split at an internal position X into a first portion (i.e., 3' portion) containing nucleotides from position X to the end of the reference RNA element, and a second portion (i.e., 5' portion) containing nucleotides from position 1 to position X-1 of the reference RNA element. Position X is referred to as the "split site" in the reference RNA element. The first portion and/or the second portion may further contain exogenous sequences that are not present in the reference RNA element. The first portion and/or the second portion may also have deletions or substitutions with respect to the sequence in the reference RNA element. The exogenous sequence(s), deletion(s) and substitutions do not substantially alter (e.g., do not reduce by more than 10%, 20%, 30%, 40%, or 50%) the functions and activities of the reconstituted RNA element by the first portion and the second portion of the RNA element.

The terms "polynucleotide," "nucleic acid," "nucleotide sequence," and "nucleic acid sequence" are used interchangeably. They refer to a polymeric form of nucleotides of any length, either deoxyribonucleotides or ribonucleotides, or analogs thereof.

The terms "deaminase-recruiting RNA," "dRNA," "ADAR-recruiting RNA" and "arRNA" are used herein interchangeably to refer to an engineered RNA capable of recruiting an Adenosine Deaminase Acting on RNA (ADAR) to deaminate a target adenosine in an RNA. Exemplary dRNAs have been described, for example, in WO2021/008447, PCT/CN2021/071292, and PCT/CN2021/113290, the contents of which are incorporated herein by reference in their entirety.

As used herein, "guide RNA" and "gRNA" are used herein interchangeably to refer to RNA that is capable of forming a complex with a Cas protein and a target nucleic acid (e.g., duplex DNA). A guide RNA may comprise a single RNA molecule or two or more RNA molecules associated with each other via hybridization of complementary regions in the two or more RNA molecules. For example, a guide RNA for a Cas9 nuclease may comprise a crRNA and a tracrRNA, and a guide RNA for a Cas12a nuclease may only comprise a crRNA. The "crRNA" or "CRISPR RNA" comprises a guide sequence that has sufficient complementarity to a target sequence of a target nucleic acid (e.g., duplex DNA), which guides sequence-specific binding of the CRISPR complex to the target nucleic acid. The "tracrRNA" or "trans-activating CRISPR RNA" is partially complementary to and base pairs with the crRNA, and may play a role in the maturation of the crRNA. A "single guide RNA" or "sgRNA" is an engineered guide RNA having both crRNA and tracrRNA fused to each other in a single molecule.

The term "therapeutic polypeptide" refers to a polypeptide having a therapeutic effect. A therapeutic polypeptide may be a naturally-occurring protein or an engineered functional variant thereof, including functional fragments, derivatives having one or more mutations (e.g., insertion, deletion, substitution, etc.) to the amino acid sequence of the naturally-occurring protein, and fusion proteins comprising a naturally-occurring protein or fragment thereof. A therapeutic polypeptide may also be an engineered protein that does not have a naturally-occurring counterpart. Therapeutic polypeptide may have a single polypeptide chain or multiple polypeptide chains.

The term "antigenic polypeptide" refers to a polypeptide that can be used to trigger the immune system of a mammal to develop antibodies specific to the polypeptide or a portion thereof. Antigenic polypeptides described herein include naturally-occurring proteins, protein domains, and short peptide fragments derived from a naturally-occurring protein. An antigenic polypeptide may contain one or more known epitopes of a naturally-occurring protein. The antigenic polypeptide may comprise a carrier protein or multimerization protein that improves immunogenicity.

The term "functional protein" refers to a naturally-occurring protein, functional variants thereof, or an engineered derivative thereof that is functional in treating a genetic disease or condition. The disease or condition may be caused in whole or in part by a change, such as a mutation, in the wildtype, naturally-occurring protein corresponding to the functional protein.

The term "targeting protein" refers to a polypeptide that specifically binds to a target molecule. Targeting proteins described herein include both antibody-based and non-antibody based binding proteins or target-binding portions thereof.

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antigen-binding fragment" as used herein refers to an antibody fragment including, for example, a diabody, a Fab, a Fab', a F(ab') 2, an Fv fragment, a disulfide stabilized Fv fragment (dsFv), a (dsFv) 2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure.

As use herein, the terms "specifically binds," "specifically recognizing," and "is specific for" refer to measurable and reproducible interactions, such as binding between a target and a targeting moiety. For example, a targeting moiety that specifically recognizes a target (which can be an epitope) is a targeting moiety (e.g., antibody) that binds this target with greater affinity, avidity, more readily, and/or with greater duration than its bindings to other molecules. In some embodiments, the extent of binding of a targeting moiety to an unrelated molecule is less than about 10% of the binding of the targeting moiety to the target as measured, e.g., by a radioimmunoassay (RIA). In some embodiments, a targeting moiety that specifically binds a target has a dissociation constant (KD) of $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. In some embodiments, specific binding can include, but does not require exclusive binding. Binding specificity of the targeting moiety can be determined experimentally by methods known in the art. Such methods comprise, but are not limited to Western blots, ELISA, RIA, ECL, IRMA, EIA, BIA-CORE™ and peptide scans.

The term "functional variant" of a reference protein refers to a variant polypeptide or polynucleotide derived from the reference protein or polynucleotide or a portion thereof, and the variant has substantially the same activity (e.g., binding to a target or enzymatic activity) as the reference protein or polynucleotide. "Substantially the same activity" means an activity level that is at least about any one of 20%, 30%, 40%, 50%, 60%, 70%, 80%, 90%, or more as the activity of the reference protein or polynucleotide.

The term "introducing" or "introduction" used herein means delivering one or more polynucleotides, such as circRNAs or one or more constructs including vectors as described herein, one or more transcripts thereof, to a host cell. The methods of the present application can employ many delivery systems, including but not limited to, viral, liposome, electroporation, microinjection and conjugation, to achieve the introduction of the circRNA or construct as described herein into a host cell. Conventional viral and non-viral based gene transfer methods can be used to introduce nucleic acids into mammalian cells or target tissues. Such methods can be used to administer nucleic acids encoding the circRNA of the present application to cells in culture, or in a host organism. Non-viral vector delivery systems include DNA plasmids, RNA (e.g. a transcript of a construct described herein), naked nucleic acid, and nucleic acid complexed with a delivery vehicle, such as a liposome. Viral vector delivery systems include DNA and RNA viruses, which have either episomal or integrated genomes for delivery to the host cell.

As used herein, "operably linked," when referring to a first nucleic acid sequence that is operably linked with a second nucleic acid sequence, means a situation when the first nucleic acid sequence is placed in a functional relationship with the second nucleic acid sequence. For instance, a promoter is operably linked to a coding sequence if the promoter effects the transcription of the coding sequence. Likewise, the coding sequence of a signal peptide is operably linked to the coding sequence of a polypeptide if the signal peptide effects the extracellular secretion of that polypeptide. Generally, operably linked nucleic acid sequences are contiguous and, where necessary to join two protein coding regions, the open reading frames are aligned.

As used herein, "complementarity" refers to the ability of a nucleic acid to form hydrogen bond(s) with another nucleic acid by traditional Watson-Crick base-pairing. A percent complementarity indicates the percentage of residues in a nucleic acid molecule which can form hydrogen bonds (i.e., Watson-Crick base pairing) with a second nucleic acid (e.g., about 5, 6, 7, 8, 9, 10 out of 10, being about 50%, 60%, 70%, 80%, 90%, and 100% complementary respectively). "Perfectly complementary" means that all the contiguous residues of a nucleic acid sequence form hydrogen bonds with the same number of contiguous residues in a second nucleic acid sequence. "Substantially complementary" as used herein refers to a degree of complementarity that is at least about any one of 70%, 75%, 80%, 85%, 90%, 95%, 97%, 98%, 99%, or 100% over a region of about 40, 50, 60, 70, 80, 100, 150, 200, 250 or more nucleotides, or refers to two nucleic acids that hybridize under stringent conditions.

As used herein, "treatment" or "treating" is an approach for obtaining beneficial or desired results including clinical results. For purposes of this application, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

The terms "individual," "subject" and "patient" are used interchangeably herein to describe a mammal, including humans. In some embodiments, the individual is human. In some embodiments, the individual is a rodent, such as a mouse. In some embodiments, the individual suffers from a genetic disease or condition. In some embodiments, the individual suffers from a coronavirus infection. In some embodiments, the individual is at risk of contracting a coronavirus infection. In some embodiments, the individual is in need of treatment.

As is understood in the art, an "effective amount" refers to an amount of a composition sufficient to produce a desired therapeutic outcome (e.g., stimulating the production of antibodies and improving immunity against one or more coronaviruses, reducing the severity or duration of, stabilizing the severity of, or eliminating one or more symptoms of a disease or condition). For therapeutic use, beneficial or desired results include, e.g., decreasing one or more symptoms resulting from the disease (biochemical, histologic and/or behavioral), including its complications and intermediate pathological phenotypes presented during development of the disease, increasing the quality of life of those suffering from the disease, decreasing the dose of other medications required to treat the disease, enhancing effect of another medication, delaying the progression of the disease, and/or prolonging survival of patients. In some embodiments, an effective amount of the therapeutic agent may extend survival (including overall survival and progression free survival); result in an objective response (including a complete response or a partial response); relieve to some extent one or more signs or symptoms of the disease or condition; and/or improve the quality of life of the subject. In some embodiments, an effective amount is a prophylactically effective amount, which is an amount of a composition sufficient to prevent or reduce the severity of one or more future symptoms of a disease or condition when administered to an individual who is susceptible and/or who may develop the disease or condition. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotypes presenting during future development of the disease).

As used herein the term "wild type" is a term of the art understood by skilled persons and means the typical form of an organism, strain, gene or characteristic as it occurs in nature as distinguished from mutant or variant forms.

The present disclosure provides several types of compositions that are polynucleotide or polypeptide based, including variants and derivatives. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular, the polypeptide sequences disclosed herein, are included within the scope of this disclosure. For example, sequence tags or amino acids can be added to peptide sequences (e.g., at the N-terminal or C-terminal ends). Sequence tags can be used for peptide detection, purification or localization. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide" or "peptide" are used herein to encompass all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

A "pharmaceutically acceptable carrier" refers to one or more ingredients in a pharmaceutical formulation, other than an active ingredient, which is nontoxic to a subject. A pharmaceutically acceptable carrier includes, but is not limited to, a buffer, excipient, stabilizer, cryoprotectant, tonicity agent, preservative, and combinations thereof. Pharmaceutically acceptable carriers or excipients have preferably met the required standards of toxicological and manufacturing testing and/or are included on the Inactive Ingredient Guide prepared by the U.S. Food and Drug administration or other state/federal government or listed in the U.S. Pharmacopeia or other generally recognized pharmacopeia for use in mammals, and more particularly in humans.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or condition (e.g., coronavirus infection), or a probe for specifically detecting a biomarker described herein. In certain embodiments, the manufacture or kit is promoted, distributed, or sold as a unit for performing the methods described herein.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat disease of type X means the method is used to treat disease of types other than X.

The term "about X-Y" used herein has the same meaning as "about X to about Y."

As used herein and in the appended claims, the singular forms "a," "an," or "the" include plural referents unless the context clearly dictates otherwise.

The term "and/or" as used herein a phrase such as "A and/or B" is intended to include both A and B; A or B; A (alone); and B (alone). Likewise, the term "and/or" as used herein a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Linear RNA and Constructs

The present application provides linear RNA precursors (also referred herein as linear RNAs) and constructs for preparing circular RNAs (circRNAs) encoding polypeptides, such as therapeutic polypeptides. A linear RNA precursor described herein comprises two split portions of an RNA element flanking an effector RNA (e.g., coding RNA) sequence. A circRNA can be obtained by ligating the ends of the split portions of the RNA element using a RNA ligase. The linear RNA may comprise any one of the first portions and second portions of the RNA elements described in Section A "RNA element" and any one of the effector RNA sequences described in Section B "Effector RNA sequence."

In some embodiments, there is provide a linear RNA, comprising from the 5' end to the 3' end: (a) a first portion of a RNA element; (b) an effector RNA sequence; and (c) a second portion of the RNA element; wherein the first portion of the RNA element and the second portion of the RNA element associate with each other to form a double-stranded region of at least 4 basepairs (bp) long (e.g., about 6-25 bp long); wherein the 5' end of the first portion of the RNA element and the 3' end of the second portion of the RNA element form a nick in the double-stranded region; and wherein the nick can be ligated by a RNA ligase. In some embodiments, the double-stranded region has a minimum free energy of no more than about −8 kcal/mol at 37° C. and an ionic strength of 1.0M Na, e.g., as predicted by RNAfold or Mfold. In some embodiments, the RNA element is at least about 20 nt (e.g., at least 50 nt, or about 20-1000 nt) long. In some embodiments, the double-stranded region comprises at least 2 bp 3' to the nick. In some embodiments, the double-stranded region comprises at least 2 (e.g., at least 4) bp 5' to the nick. In some embodiments, the RNA element is a naturally occurring RNA element or a derivative thereof. In some embodiments, the RNA element is a sgRNA. In some embodiments, the RNA element is an H/ACA box snoRNA. In some embodiments, the effector RNA sequence is about 50 nt to about 5000 nt long. In some embodiments, the effector RNA sequence is a sequence of a non-coding RNA selected from the group consisting of a guide RNA (gRNA), a deaminase-recruiting RNA (dRNA), a siRNA, a miRNA, a shRNA, and a long intervening non-coding (line) RNA.

In some embodiments, there is provide a linear RNA, comprising from the 5' end to the 3' end: (a) a first portion of a RNA element; (b) a coding RNA sequence; and (c) a second portion of the RNA element; wherein the first portion of the RNA element and the second portion of the RNA element associate with each other to form a double-stranded region of at least 4 basepairs (bp) long (e.g., about 6-25 bp long); wherein the 5' end of the first portion of the RNA element and the 3' end of the second portion of the RNA element form a nick in the double-stranded region; and wherein the nick can be ligated by a RNA ligase. In some embodiments, the double-stranded region has a minimum free energy of no more than about −8 kcal/mol at 37° C. and an ionic strength of 1.0M Na, e.g., as predicted by RNAfold or Mfold. In some embodiments, the RNA element is at least about 20 nt (e.g., at least 50 nt, or about 20-1000 nt) long. In some embodiments, the double-stranded region comprises at least 2 bp 3' to the nick. In some embodiments, the double-stranded region comprises at least 2 (e.g., at least 4) bp 5' to the nick. In some embodiments, the RNA element is a naturally occurring RNA element or a derivative thereof. In some embodiments, the RNA element promotes translation of the coding RNA sequence. In some embodiments, the coding RNA sequence is about 50 nt to about 5000 nt long. In some embodiments, the coding RNA sequence encodes a therapeutic polypeptide, such as an antigenic polypeptide, a functional protein, a receptor protein, or a targeting protein.

In some embodiments, there is provide a linear RNA, comprising from the 5' end to the 3' end: (a) a first portion of a RNA element; (b) an effector RNA (e.g., coding RNA) sequence; and (c) a second portion of the RNA element; wherein the first portion of the RNA element and the second portion of the RNA element are derived from a reference RNA element of N nucleotides, wherein N is an integer greater than 8; wherein the first portion of the RNA element comprises nucleotides X to N of the reference RNA element, wherein X is an integer greater than 1 and smaller than N; and wherein the second portion of the RNA element comprises nucleotides 1 to X-1 of the reference RNA element; wherein the first portion of the RNA element and the second portion of the RNA element associate with each other to form a double-stranded region of at least 4 basepairs (bp) long (e.g., about 6-25 bp long); wherein the 5' end of the first portion of the RNA element and the 3' end of the second portion of the RNA element form a nick in the double-stranded region; and wherein the nick can be ligated by a RNA ligase. In some embodiments, the double-stranded region has a minimum free energy of no more than about −8 kcal/mol at 37° C. and an ionic strength of 1.0M Na, e.g., as predicted by RNAfold or Mfold. In some embodiments, the RNA element is at least about 20 nt (e.g., at least 50 nt, or about 20-1000 nt) long. In some embodiments, the double-stranded region comprises at least 2 bp 3' to the nick. In some embodiments, the double-stranded region comprises at least 2 (e.g., at least 4) 5' to the nick. In some embodiments, the first portion of the RNA element and/or the second portion of the RNA element comprises a sequence that is exogenous to the reference RNA element. In some embodiments, the second portion of the RNA element comprises a first exogenous sequence at the 3' end, wherein the first portion of the RNA element comprises a second exogenous sequence that is complementary of the first exogenous sequence, and wherein the first exogenous sequence and the second exogenous sequence form base pairs flanking the 5' end of the nick. In some embodiments, the first exogenous sequence is GUUU. In some embodiments, the RNA element is a naturally occurring RNA element or a derivative thereof. In some embodiments, the effector RNA sequence is a coding RNA sequence. In some embodiments, the effector RNA sequence is about 50 nt to about 5000 nt long. In some embodiments, the RNA element promotes translation of the coding RNA sequence. In some embodiments, the coding RNA sequence encodes a therapeutic polypeptide, such as an antigenic polypeptide, a functional protein, a receptor protein, or a targeting protein.

In some embodiments, there is provided a linear RNA, comprising from the 5' end to the 3' end: (a) a first portion of an internal ribosomal entry site (IRES); (b) a coding RNA sequence; and (c) a second portion of the IRES; wherein the first portion of the IRES and the second portion of the IRES associate with each other to form a double-stranded region of at least 4 bp (e.g., about 6-25 bp) long; wherein the 5' end of the first portion of the IRES and the 3' end of the second portion of the IRES form a nick in the double-stranded region; and wherein the nick can be ligated by a RNA ligase. In some embodiments, the double-stranded region has a minimum free energy of no more than about −8 kcal/mol at 37° C. and an ionic strength of 1.0M Na, e.g., as predicted by RNAfold or Mfold. In some embodiments, the double-stranded region comprises at least 2 bp 3' to the nick. In some embodiments, the double-stranded region comprises at least 2 (e.g., at least 4) 5' to the nick. In some embodiments, the first portion of the IRES and the second portion of the IRES are derived from a reference IRES of N nucleotides, wherein N is an integer greater than 8; wherein the first portion of the IRES comprises nucleotides X to N of the reference IRES, wherein X is an integer greater than 1 and smaller than N; and wherein the second portion of the IRES comprises nucleotides 1 to X-1 of the reference IRES. In some embodiments, the first portion of the IRES and/or the second portion of the IRES comprises a sequence that is exogenous to the reference IRES. In some embodiments, the second portion of the IRES comprises a first exogenous sequence at the 3' end, wherein the first portion of the IRES comprises a second exogenous sequence that is complementary of the first exogenous sequence, and wherein the first exogenous sequence and the second exogenous sequence form base pairs flanking the 5' end of the nick. In some embodiments, the first exogenous sequence is GUUU. In some embodiments, IRES is derived from an IRES from a virus selected from the group consisting of CVB3, EV71, EMCV, PV, HCV, AdV, HPV31, HHV, RSV, and CSFV. In some embodiments, the IRES is derived from a human IRES, such as FGF9 IRES, SLC7A1 IRES or RUNX1 IRES. In some embodiments, the coding RNA sequence is about 50 nt to about 5000 nt long. In some embodiments, the coding RNA sequence encodes a therapeutic polypeptide, such as an antigenic polypeptide, a functional protein, a receptor protein, or a targeting protein.

In some embodiments, there is provided a linear RNA, comprising from the 5' end to the 3' end: (a) a first RNA portion comprising nucleotides 382-741 of a CVB3 IRES, wherein the nucleotide numbering is according to SEQ ID NO: 1; (b) a coding RNA sequence; and (c) a second RNA portion comprising nucleotides 1-381 of a CVB3 IRES; wherein the first RNA portion and the second RNA portion associate with each other to form a double-stranded region comprising a nick formed by the 5' end of the first RNA portion and the 3' end of the second RNA portion; and wherein the nick can be ligated by a RNA ligase. In some embodiments, the first RNA portion and/or the second RNA portion comprises a sequence that is exogenous to the CVB3 IRES. In some embodiments, the second RNA portion comprises a first exogenous sequence at the 3' end, wherein the first RNA portion comprises a second exogenous sequence that is complementary of the first exogenous sequence, and wherein the first exogenous sequence and the second exogenous sequence form base pairs flanking the 5' end of the nick. In some embodiments, the first exogenous sequence is GUUU. In some embodiments, the first RNA portion comprises the nucleotide sequence of SEQ ID NO: 3, and wherein the second RNA portion comprises the nucleotide sequence of SEQ ID NO: 2. In some embodiments, the coding RNA sequence is about 50 nt to about 5000 nt long. In some embodiments, the coding RNA sequence encodes a therapeutic polypeptide, such as an antigenic polypeptide, a functional protein, a receptor protein, or a targeting protein.

In some embodiments, the linear RNA comprises, from 5' to 3' end, a first portion of IRES, an optional signal peptide, a coding RNA sequence, a sequence encoding a 2A peptide, and a second portion of IRES. In some embodiments, the linear RNA sequence can be obtained by transcribing the DNA nucleotide sequence of SEQ ID NO: 10 or 11.

In some embodiments, there is provided a nucleic acid construct comprising a nucleic acid sequence encoding any one of the linear RNAs described herein. In some embodiments, a T7 promoter is operably linked to the nucleic acid sequence encoding the linear RNA. In some embodiments, the T7 promoter comprises the sequence set forth in SEQ ID NO: 6. In some embodiments, the T7 promoter is capable of driving in vitro transcription.

In some embodiments, the nucleic acid construct is a plasmid. In some embodiments, the plasmids are obtained by cloning the sequence encoding the linear RNAs into a plasmid vector. Plasmids can be generated by techniques known in the art, such as Gibson cloning or cloning using restriction enzymes. In some embodiments, the plasmid vector includes an antibiotic expression cassette allowing antibiotic selection of bacteria expressing the plasmid. In some embodiments, the plasmids provided can be purified from bacteria and used for production of the linear RNA constructs. Any plasmid vector suitable for in vitro transcription of the linear RNA may be used. In some embodiments, the plasmids are linearized prior to in vitro transcription of the linear RNA. In some embodiments, the recombinant plasmids are linearized by restriction enzyme digestion. In some embodiments, the recombinant plasmids are linearized by PCR amplification.

A. RNA Element

The linear RNAs described herein comprise split portions of an RNA element that has extensive secondary structures, including double-stranded helical regions. Split portions (i.e., first portion and second portion) can be engineered based on a reference RNA element by dividing the reference RNA element into a 5' portion (i.e., the second portion in the linear RNA described herein) and a 3' portion (i.e., the first portion in the linear RNA described herein) at a "split site", i.e., a phosphodiester bond 5' to a nucleotide, in a stable double-stranded region of the reference RNA element. For example, if the split site is 5' to nucleotide X in an RNA element having N nucleotides, wherein X and N are integers and X is greater than 1 and smaller than N, then the first portion of the RNA element comprises nucleotides 1 to X-1 of the RNA element, and the second portion of the RNA element comprises nucleotides X to N of the RNA element. The split portions can be further engineered by introducing one or more exogenous sequence(s) into the first portion and/or the second portion of the RNA element, deleting one or more nucleotides in the first portion and/or the second portion of the RNA element, and/or substituting one or more nucleotides in the first portion and/or the second portion of the RNA element. The split portions of the RNA element in a linear RNA are capable of associating with each other to reconstitute the double-stranded region, while the 5' end of the first portion and the 3' end of the second portion give rise to a nick at the split site that can be ligated by a RNA ligase (e.g., T4 RNA ligase 1 or T4 RNA ligase 2).

Figure 2A:
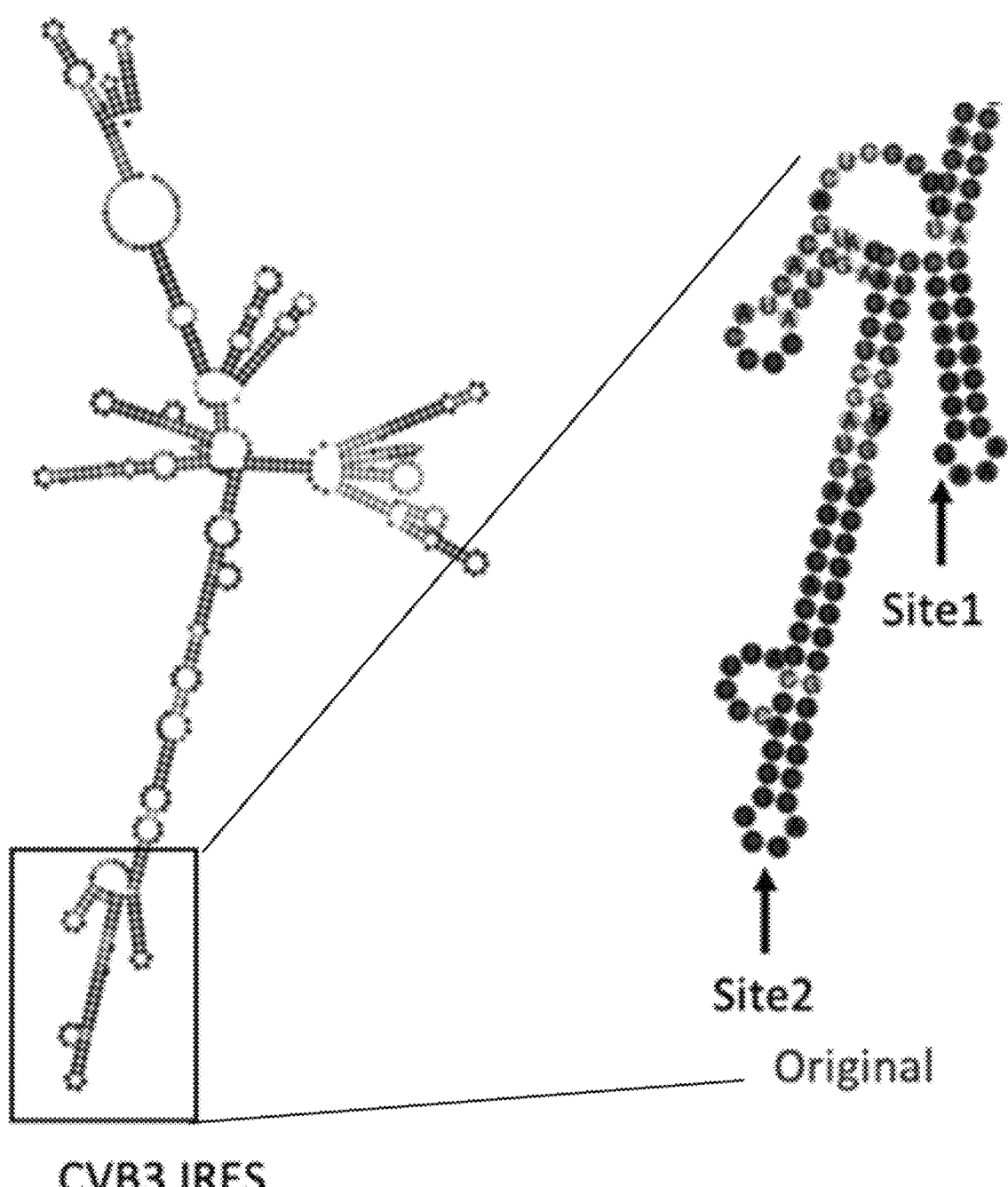
FIG. 2A shows the secondary structure of a wildtype CVB3 IRES as predicted by RNAfold. Each circle in the structure represents a nucleotide. The boxed region (also referred herein as the "engineered CVB3 IRES region"; residues 282-402 of SEQ ID NO:1) represents a region in the CVB3 IRES having highly stable double-stranded structures, which could promote formation of intramolecular double strands. This region is enlarged in the right hand side of the figure. Linear RNA constructs with two engineered IRES split portions having split sites within Site 1 and Site 2, respectively, were designed for production of circular RNA via ligation of the engineered IRES split portions by a T4 RNA ligase.

The split site in an RNA element can be chosen by first identifying a stable double-stranded region so that when the RNA element is split into two portions, which are placed at two ends of an effector RNA (e.g., coding RNA) sequence in a linear RNA, the two portions can associate to form a double-stranded region with a nick. The low free energy of the double-stranded region promotes intramolecular ligation by a RNA ligase. Stable double-stranded regions in an RNA element can be identified computationally using known methods in the art. For example, RNAfold (Hofacker, I. L. Vienna RNA secondary structure server. Nucleic Acids Res. 31, 3429-3431 (2003)) and Mfold (M. Zuker, Nucleic Acids Res., 31 (13), 3406-15, (2003)) are web servers that can be used to computationally fold RNA molecules and predict secondary structures, including double-stranded regions, in RNA molecules. For example, FIG. 2A shows the secondary structure of CVB3 IRES as predicted by RNAfold. A region with low free energy and double-stranded helical regions can be chosen, such as the boxed region of FIG. 2A, to engineer a split site within a double-stranded region, for example, at site 1 and site 2 as shown in FIG. 2A. The split site should not be adjacent to nucleotide positions that are known to affect the function of the RNA element. In some embodiments, a phosphodiester bond in the RNA element that can be easily accessed is chosen as the split site. In some embodiments, the double-stranded region has a high GC content, such as at least about any one of 40%, 50%, 60%, 70%, 80%, or higher GC basepairs.

In some embodiments, the split site is chosen close to the midpoint of the reference RNA element. In some embodiments, the first portion of the RNA element has substantially the same length as the second portion of the RNA element. For example, the length of the first portion of the RNA element differs from the length of the second portion of the RNA element by no more than about any one of 100, 90, 80, 70, 60, 50, 40, 30, 20, 10, 5 or fewer nucleotides. In some embodiments, the length of the first portion of the RNA element differs from the length of the second portion of the RNA element by no more than about any one of 20%, 15%, 10%, 5%, or less.

In some embodiments, the split site is chosen in a double-stranded region that is at least 4 bp long, such as at least about any one of 4, 5, 6, 7, 8, 9, 10, 11, 12, 13, 14, 15, 16, 17, 18, 19, 20, 21, 22, 23, 24, 25 or more bp long. In some embodiments, the double-stranded region is about any one of 4, 5, 6, 7, 8, 9, 10, 11, 12, 13, 14, 15, 16, 17, 18, 19, 20, 21, 22, 23, 24, or 25 bp long. In some embodiments, the double-stranded region is no more than about any one of 25, 24, 23, 22, 21, 20, 19, 18, 17, 16, 15, 14, 13, 12, 11, 10, 9, 8, 7, or 6 bp long. In some embodiments, the double-stranded region is about any one of 4-25, 4-15, 4-10, 6-25, 6-15, 6-10, 10-15, 10-20, or 10-25 bp. In some embodiments, the double-stranded region is about 6 bp to about 25 bp long. In some embodiments, the double-stranded region is part of a stem loop. In some embodiments, the double-stranded region is a helix. In some embodiments, the double-stranded region further comprises a bulge.

In some embodiments, the double-stranded region has a minimum free energy of no more than about $-5$ kcal/mol, such as no more than about any one of $-5.5$, $-6$, $-6.5$, $-7$, $-7.5$, $-8$, $-8.5$, $-9$, $-9.5$, $-10$, $-10.5$, $-11$, $-11.5$, $-12$, $-12.5$, $-13$, $-14$, $-15$ kcal/mol or lower, as predicted by RNAfold or Mfold. In some embodiments, the double-stranded region has a minimum free energy of about any one of $-15$ to $-5.5$, $-10$ to $-5.5$, $-8$ to $-5.5$, $-15$ to $-8$, $-12$ to $-8$, or $-10$ to $-8$ kcal/mol. In some embodiments, the minimum free energy of the RNA element is no more than about any one of $-50$, $-100$, $-150$, $-200$, $-250$, $-300$ kcal/mol or lower.

In some embodiments, the RNA element is at least 20 nt long, such as at least about any one of 50, 75, 100, 150, 200, 250, 300, 350, 400, 450, 500, 550, 600, 650, 700, 750, 800, 900 or more nt long. In some embodiments, the RNA element is no more than about any one of 1000, 900, 800, 750, 700, 650, 600, 550, 500, 450, 400, 350, 300, 250, 200, 150, 100, 75, 50 or 20 nt long. In some embodiments, the RNA element is about any one of 20-50, 50-100, 20-200, 20-300, 20-500, 20-1000, 50-200, 50-1000, 100-1000, 100-500, 200-500, 200-1000, 300-1000, 300-800, 400-900, or 500-1000 nt long.

As shown in FIG. 1, in an exemplary linear RNA, the first portion of the RNA element flanks the 5' end of an effector RNA (e.g., coding RNA), and the second portion of the RNA element flanks the 3' end of the coding RNA (e.g., coding RNA). The first portion of the RNA element self-assemble with the second portion of the RNA element for form a double-stranded region with a nick at the split site, which serves as a substrate of a RNA ligase. In some embodiments, basepairs immediately adjacent to the 5' and/or 3' side of the nick promotes ligation of the nick by a RNA ligase. In some embodiments, the double-stranded region comprises at least 2 bp, such as 2, 3, 4, 5, 6, or more bp, 3' to the nick. In some embodiments, the double-stranded region comprises at least 2 bp, such as 2, 3, 4, 5, 6, 7, 8, 9, 10, or more bp, 5' to the nick.

In some embodiments, the first portion of the RNA element and the second portion of the RNA element are derived from a reference RNA element of N nucleotides, wherein N is an integer greater than 8; wherein the first portion of the RNA element comprises nucleotides X to N of the reference RNA element, wherein X is an integer greater than 1 and smaller than N; and wherein the second portion of the RNA element comprises nucleotides 1 to X-1 of the reference RNA element. In some embodiments, the first portion of the RNA element consists of or consists essentially of nucleotides X to N of the reference RNA element, and wherein the second portion of the RNA element consists of or consists essentially of nucleotides 1 to X-1 of the reference element.

In some embodiments, compared to the reference RNA element, the RNA element has no exogenous sequence. In some embodiments, the RNA element reconstituted by ligating the 5' end of the first portion of the RNA element and the 3' end of the second portion of the RNA element is identical to the reference RNA element.

In some embodiments, the RNA element after ligation of the nick is a portion of the reference RNA element. The portion contains the stable double-stranded region. The portion may or may not have the function of the reference RNA element.

In some embodiments, the RNA element after ligation of the nick contains all nucleotides of the reference RNA element. In some embodiments, the RNA element after ligation of the nick is the reference RNA element.

In some embodiments, compared to the reference RNA element, the RNA element comprises one or more exogenous sequences. In some embodiments, the first portion of the RNA element comprises a sequence that is exogenous to the reference RNA element. In some embodiments, the second portion of the RNA element comprises a sequence that is exogenous to the reference RNA element. In some embodiments, the first portion of the RNA element comprises a first sequence that is exogenous to the reference RNA element, and the second portion of the RNA element comprises a second sequence that is exogenous to the reference RNA element.

For example, exogenous sequences can be introduced to the first portion of the RNA element or the second portion of the RNA element in order to further stabilize the double-stranded region comprising the nick, thereby promoting ligation of the nick by a RNA ligase. In some embodiments, the first portion of the RNA element comprises a first exogenous sequence at the 3' end and the second portion of the RNA element comprises a second exogenous sequence that is complementary to the first exogenous sequence, wherein the first exogenous sequence and the second exogenous sequence form basepairs flanking the 5' end of the nick. In some embodiments, the first exogenous sequence and the second exogenous sequence are each at least 4 nt long, such as about any one of 4, 5, 6, 7, 8, or more nt long. In some embodiments, the first exogenous sequence is GUUU, and the second exogenous sequence is AAAC.

The RNA element can be a naturally occurring RNA element, such as a regulatory RNA element, a derivative thereof, or an artificial RNA element. In some embodiments, the RNA element is a cis-regulatory RNA element.

In some embodiments, the RNA element is a regulatory RNA element that promotes translation of the coding RNA sequence. In some embodiments, the RNA element is an internal ribosomal entry site (IRES). In some embodiments, the RNA element is a full-length IRES. In some embodiments, the RNA element is a portion of an IRES comprising the stable double-stranded region. The portion of IRES may not be functional for promoting protein translation.

Figure 6:
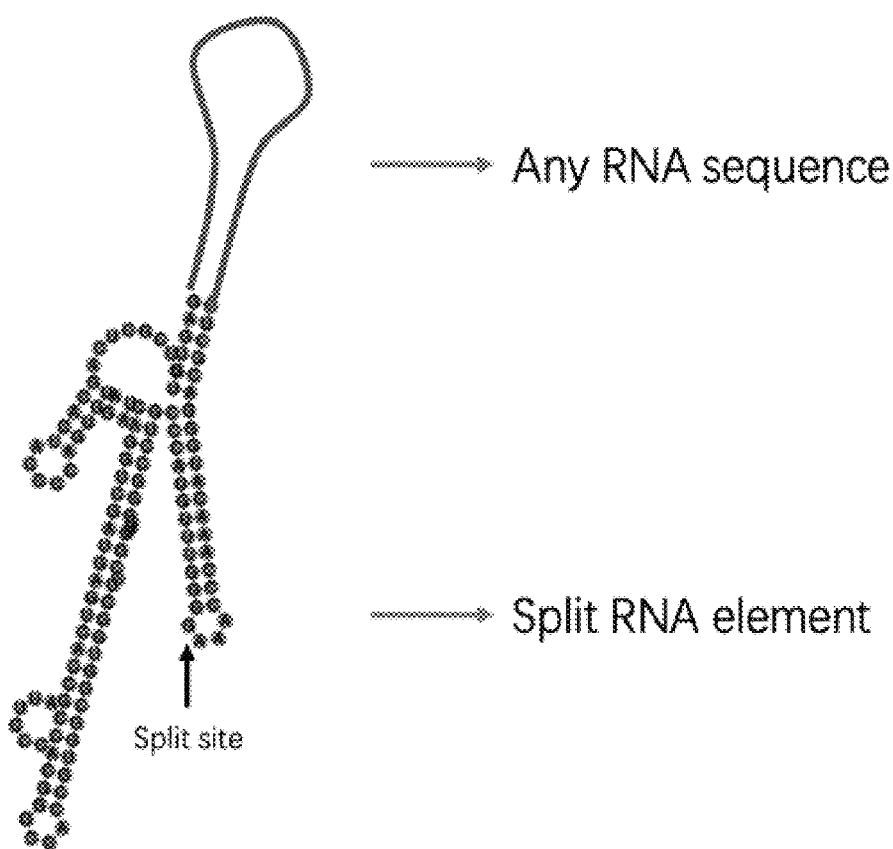
FIG. 6 shows a linear RNA precursor comprising split IRES portions flanking an effector RNA sequence. The split IRES (residues 282-402 of SEQ ID NO:1) portions reconstitute only a portion of a naturally occurring IRES.

For example, as shown in FIG. 6, in an exemplary linear RNA, the first portion and the second portion are derived from a stem loop portion of a CVB3 IRES which contains a highly stable double-stranded region. The first portion and the second portion flank an effector RNA sequence, which may be a coding RNA or a non-coding RNA (such as a gRNA, a dRNA, a miRNA, a siRNA, a shRNA, or a lincRNA).

In some embodiments, the IRES is a viral IRES sequence. In non-limiting examples, the IRES sequence can be an IRES from a virus selected from the group consisting of CVB3, EV71, EMCV, PV, HCV, AdV, HPV31, HHV, RSV, and CSFV. See, for example, "Searching for IRES," RNA. 2006 October; 12 (10): 1755-1785, which is incorporated herein by reference in its entirety. In some embodiments, the IRES sequence is a cellular IRES sequence. In some embodiments, the IRES is derived from a human IRES, such as FGF9 IRES, SLC7A1 IRES or RUNX1 IRES. Exemplary IRES sequences can be found at databases, such as reprod.njmu.edu.cn/cgi-bin/iresbase/view_eukaryote.php, and cobishss0.im.nuk.edu.tw/Human_IRES_Atlas/, which are incorporated herein by reference in their entirety.

Figures 2B, 2C:
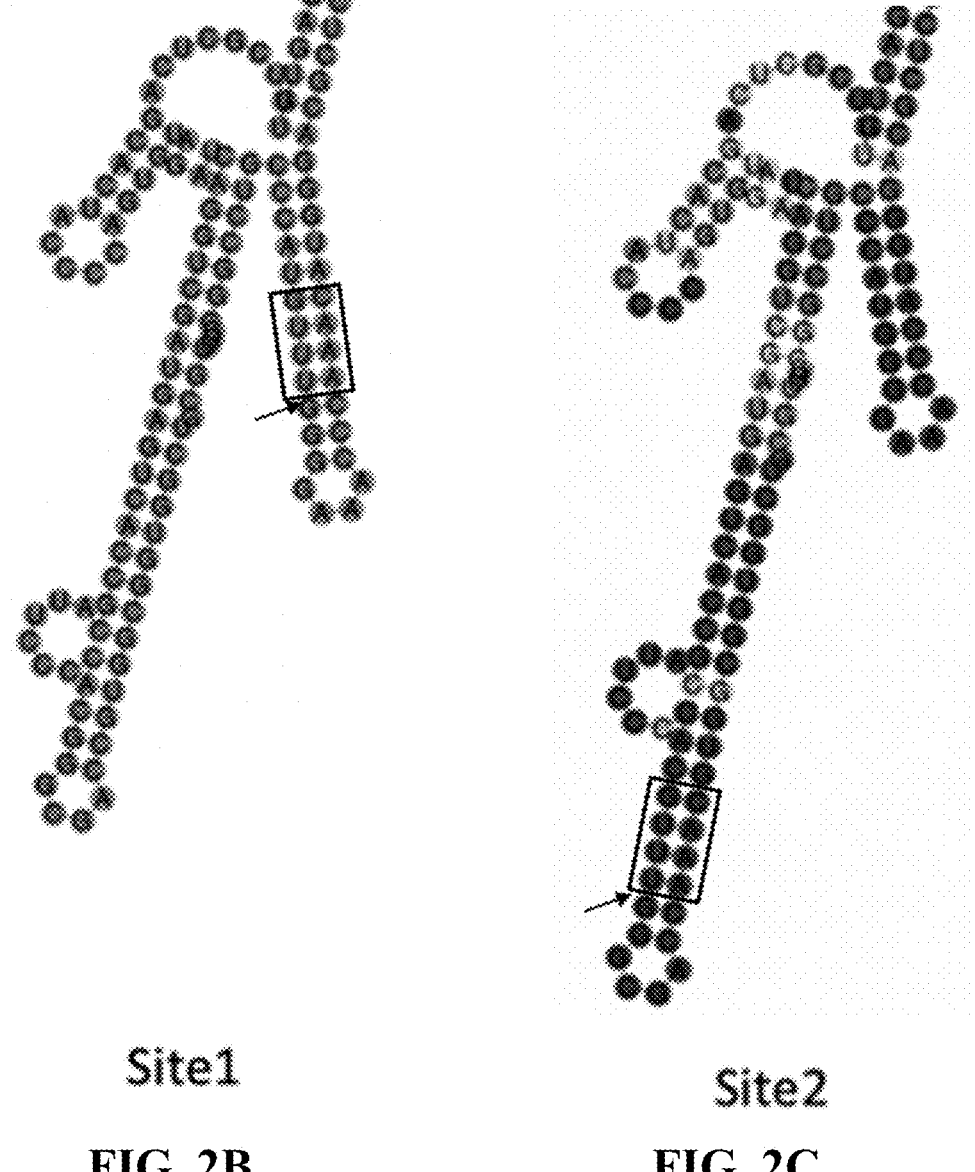
FIG. 2B shows the predicted secondary structure of the engineered CVB3 IRES region (residues 282-402 of SEQ ID NO:1) in a first exemplary pair of engineered IRES split portions having the split site at Site 1 in a linear RNA transcript. The ligation site is marked with an arrow, and four nucleotides GUUU and its reverse complementary sequence were added in the engineered IRES split portions immediately neighboring the ligation site.
FIG. 2C shows the predicted secondary structure of the engineered CVB3 IRES region (residues 282-402 of SEQ ID NO:1) in a first exemplary pair of engineered IRES split portions having the split site at Site 2 in a linear RNA transcript. The ligation site is marked with an arrow, and four nucleotides GUUU and its reverse complementary sequence were added in the engineered IRES split portions immediately neighboring the ligation site.

In some embodiments, the RNA element is an IRES of a CVB3 virus or a derivative thereof. An exemplary sequence of a CVB3 IRES is SEQ ID NO: 1. The secondary structure of CVB3 IRES predicted by RNAfold is shown in FIG. 2. The CVB3 IRES can be split at two different split sites within stable double-stranded regions. Split site 1 is 5' to nucleotide 382, wherein the numbering is based on SEQ ID NO: 1. In some embodiments, the first portion of the RNA element comprises nucleotides 382-741 of SEQ ID NO: 1, and the second portion of the RNA element comprises nucleotides 1-381 of SEQ ID NO: 1. In some embodiments, the first portion of the RNA element comprises the nucleotide sequence of SEQ ID NO: 3, and the second portion of the RNA element comprises the nucleotide sequence of SEQ ID NO: 2. Split site 2 is 5' to nucleotide 343, wherein the numbering is based on SEQ ID NO: 1. In some embodiments, the first portion of the RNA element comprises nucleotides 343-741 of SEQ ID NO: 1, and the second portion of the RNA element comprises nucleotides 1-342 of SEQ ID NO: 1. In some embodiments, the first portion of the RNA element comprises the nucleotide sequence of SEQ ID NO: 5, and the second portion of the RNA element comprises the nucleotide sequence of SEQ ID NO: 4.

Figure 7:
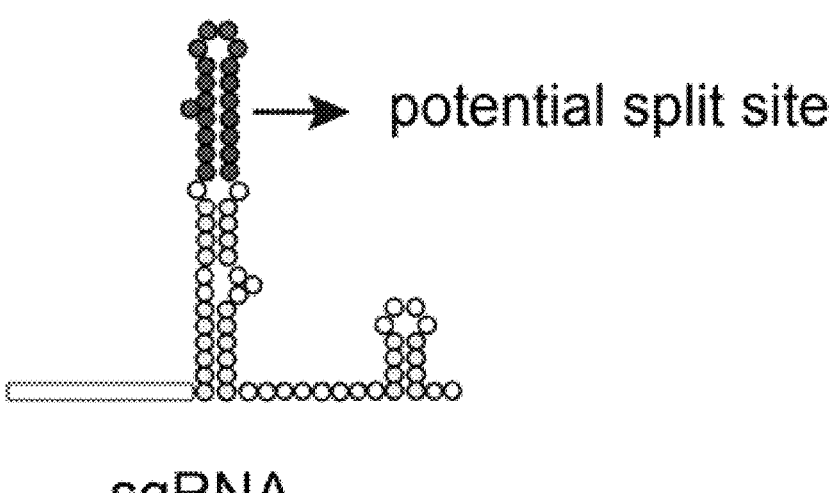
FIG. 7 shows the secondary structure of an exemplary sgRNA and a potential split site.

In some embodiments, the RNA element is a guide RNA, such as a single guide RNA (sgRNA) that is operable with a Cas nuclease. In some embodiments, the gRNA or sgRNA is for gene editing. Exemplary Cas nucleases include, but are not limited to, Cas9, Cas12a, Cas12b, Cas12c, Cas12d, Cas12f, Cas12g, Cas12h, Cms1, Cas12i, Cas12j, Cas12k and CasX. FIG. 7 shows a potential split site in a sgRNA. In some embodiments, wherein the RNA element is a gRNA (e.g., sgRNA), the effector RNA encodes a Cas nuclease (e.g., Cas9).

Figure 8:
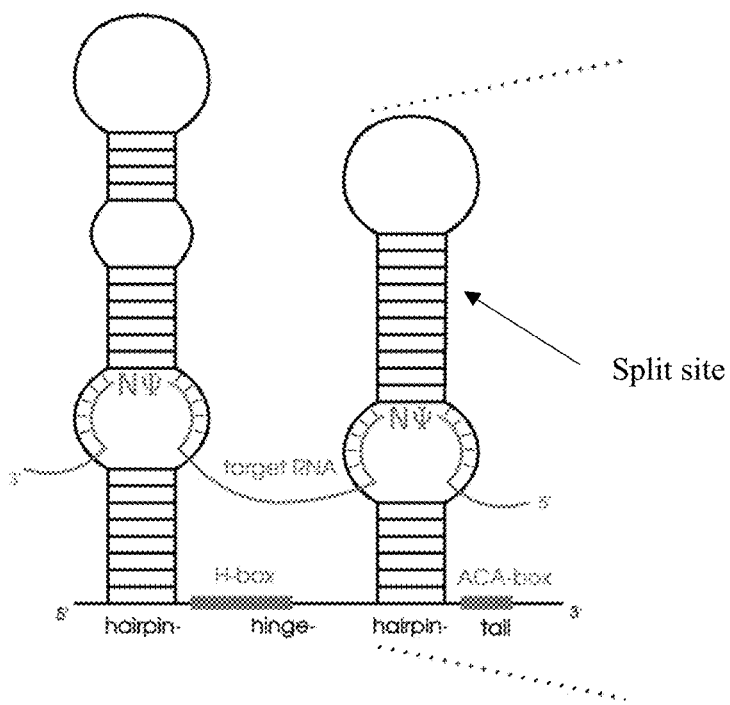
FIG. 8 shows the secondary structure of an exemplary H/ACA box snoRNA bound to a target RNA, and a potential split site.

In some embodiments, the RNA element is a small nucleolar RNA (snoRNA) or a portion thereof. In some embodiments, the RNA element is an H/ACA box of a snoRNA. H/ACA box snoRNAs have a common secondary structure consisting of two hairpins and two single-stranded regions. FIG. 8 shows a potential split site in a H/ACA snoRNA. Exemplary H/ACA snoRNA sequences can be found in snoStrip Webserver at snostrip.bioinf.uni-leipzig.de. The H/ACA snoRNA may be used to convert a uridine into pseudouridine in a target RNA. H/ACA snoRNA sequences could be used for mRNA editing. See, for example, U.S. Pat. No. 8,603,457B2.

The first portion of the RNA element and the second portion of the RNA element serve as ligation sequences in the linear RNA. Other than the first portion and the second portion of the RNA element, the linear RNAs described herein have no additional sequences for ligation. In some embodiments, the linear RNA does not comprise a 5' ligation sequence at the 5' end, and a 3' ligation sequence at the 3' end, wherein the 5' ligation sequence and the 3' ligation sequence can be ligated to each other via a ligase (e.g., T4 RNA ligase) in the presence of a splint oligonucleotide that hybridizes with the 5' ligation sequence and the 3' ligation sequence.

B. Effector RNA Sequence

The linear RNA precursors and circRNAs described herein comprise an effector RNA sequence, which may be a coding RNA sequence or a non-coding RNA sequence. Exemplary non-coding RNAs include, but are not limited to, guide RNAs (gRNA, including single guide RNA or sgRNA), a deaminase-recruiting RNA (dRNA), a small RNA (such as a microRNA, a short hairpin RNA, or a small interfering RNA), or a long intervening non-coding RNA (lincRNA).

In some embodiments, the effector RNA sequence is at least about 50 nt long, such as at least about any one of 100, 150, 200, 300, 600, 900, 1200, 1500, 2000, 3000, 4000, 5000, or more nt long. In some embodiments, the effector RNA sequence is no more than about any one of 5000, 4000, 3000, 2000, 1500, 1200, 900, 600, 300, 200, 150, or 100 nt long. In some embodiments, the effector RNA sequence is about any one of 50-100, 100-500, 500-1000, 1000-2000, 2000-5000, 50-5000, 100-5000, 100-3000, 500-5000, 500-2500, 2500-5000, or 1000-5000 nt long.

In some embodiments, the effector RNA sequence is a coding RNA sequence, which encode any polypeptide of interest. In some embodiments, the polypeptide is at least about 15 amino acids long, such as at least about any one of 20, 50, 100, 200, 300, 400, 500, 600, 700, 800, 900, 1000 or more amino acids long. In some embodiments, the polypeptide is no more than about any one of 1000, 900, 800, 700, 600, 500, 400, 300, 200, 100, 50, or 20 amino acids long. In some embodiments, the polypeptide is about any one of 20-50, 50-100, 20-200, 20-500, 20-1000, 50-500, 50-1000, 100-500, 100-1000, 200-1000 or 500-1000 amino acids long.

In some embodiments, the coding RNA sequence encodes a therapeutic polypeptide. In some embodiments, the therapeutic polypeptide is an antigenic polypeptide, a functional protein, a receptor protein or a targeting protein (e.g., an antibody).

In some embodiments, the coding RNA sequence encodes an antigenic polypeptide. A circRNA vaccine may be prepared using a linear RNA comprising a coding RNA sequence encoding an antigenic polypeptide. An antigenic polypeptide comprises at least one epitope recognizable by a T cell receptor (TCR). In some embodiments, the antigenic polypeptide is a full-length protein or a fragment thereof, or an antigenic fusion protein that can trigger an immune response in a subject. In some embodiments, the antigenic polypeptide is a short peptide of no more than 100 amino acids long. The antigenic polypeptide can be a naturally derived peptide fragment from a protein antigen containing one or more epitopes, or an artificially designed peptide with one or more natural epitope sequences, wherein a peptide linker may optionally be placed in between adjacent epitope sequences. In some embodiments, the antigenic polypeptide comprises a single epitope of an antigenic protein. In some embodiments, the antigenic polypeptide comprises about any one of 1, 2, 3, 4, 5, 10 or more epitopes from a single antigenic protein. In some embodiments, the antigenic polypeptide comprises epitopes from a plurality (e.g., 2, 3, 4, 5, 10 or more) of different antigenic proteins. In some embodiments, the antigenic polypeptide comprises a Major Histocompatibility Complex (MHC) class I-restricted epitope. In some embodiments, the antigenic polypeptide comprises a MHC class II-restricted epitope. In some embodiments, the antigenic polypeptide comprises both MHC class I-restricted and MHC class II-restricted epitopes.

In some embodiments, the antigenic polypeptide is an antigenic protein or fragment thereof or a variant thereof from a pathogenic agent, such as a bacterium or a virus. In some embodiments, the antigenic polypeptide is an antigenic protein or fragment of a coronavirus, such as SARS-COV2, including variants thereof. In some embodiments, the antigenic polypeptide comprises a Spike(S) protein or a fragment thereof or a variant thereof of a coronavirus, such as SARS-COV, MERS-COV, or SARS-COV-2. CircRNA vaccines have been described, for example, in PCT/CN2021/074998, which is incorporated herein by reference in its entirety. The linear RNAs and constructs described herein may be used to prepare any one of the known circRNA vaccines in the art.

In some embodiments, the antigenic polypeptide is an antigenic protein or fragment thereof or a variant thereof of a self-antigen, such as an antigen involved in a disease or condition. In some embodiments, the antigenic polypeptide is a tumor antigen peptide. Tumor antigen peptide sequences are known in the art and can be found at public databases, such as the Cancer Antigenic Peptide Database (van der Bruggen P et al. (2013) "Peptide database: T cell-defined tumor antigens." *Cancer Immunity*. URL: caped.icp.ucl.ac.be). The coding RNA sequence in the linear RNA or circRNA described herein may encode any of the known tumor antigen peptides or combinations thereof. In some embodiments, the antigenic polypeptide comprises an epitope of a tumor associated antigen (TAA). In some embodiments, the antigenic polypeptide comprises an epitope of a tumor specific antigen. In some embodiments, the antigenic polypeptide comprises an epitope of a neoantigen, i.e., newly acquired and expressed antigens present in tumor cells of an individual.

In some embodiments, the amino acid sequences of one or more epitope peptides are predicted based on the sequence of the antigen protein (including neoantigens) using a bioinformatics tool for T cell epitope prediction. Exemplary bioinformatics tools for T cell epitope prediction are known in the art, for example, see Yang X. and Yu X. (2009) "An introduction to epitope prediction methods and software" Rev. Med. Virol. 19 (2): 77-96. In some embodiments, the sequence of the antigen protein is known in the art or available in public databases. In some embodiments, the sequence of the antigen protein (including neoantigens) is determined by sequencing a sample (such as a tumor sample) of the individual being treated.

In some embodiments, the antigenic polypeptide comprises a multimerization domain, such as a dimerization domain, a trimerization domain, or a domain that mediates formation of higher order multimers. In some embodiments, the multimerization domain is a trimerization domain. In non-limiting examples, the multimerization domain comprises a C-terminal Foldon (Fd) domain of a T4 fibritin protein, wherein the C-terminal Foldon domain is the domain that mediates trimerization of the T4 fibritin protein. In another example, the multimerization domain comprises a GCN4-based isoleucine zipper (IZ) domain based on the trimerization domain of the GCN4 transcriptional activator from Saccharomyces cerevisiae. In some embodiments, the GCN4 IZ domain or T4 fibritin Fd domain can be modified to reduce their immunogenicity according to known techniques in the art. For example, the GCN4 IZ domain can be modified with N-linked glycosylation sites to reduce its immunogenicity (Sliepen et al. Immunosilencing a Highly Immunogenic Protein Trimerization Domain. The Journal of Biol. Chem. Vol. 290, No. 12, pp. 7436-7442).

In some embodiments, the antigenic polypeptide further comprises an immunogenic carrier protein. In some embodiments, the antigenic polypeptide comprises an epitope peptide conjugated to an immunogenic carrier protein. Exemplary immunogenic carrier proteins include, but are not limited to, tetanus toxoid (TT), diphtheria toxoid (DT), modified cross-reacting material of diphtheria toxin (CRM197), meningococcal outer membrane protein complex (OMPC), and Hemophilus influenzae protein D (HiD).

In some embodiments, the coding RNA sequence encodes a targeting protein. In some embodiments, the targeting protein is an antibody or an antigen-binding fragment thereof.

In some embodiments, the coding RNA sequence encodes an antibody. In some embodiments, the therapeutic polypeptide is a neutralizing antibody, i.e., an antibody that blocks an interaction between a protein and its binding partner. In some embodiments, the antibody inhibits activity of a protein, e.g., by blocking binding of the protein to a binding partner. In some embodiments, the targeting protein is a therapeutic antibody. In some embodiments, the antibody is a checkpoint inhibitor, e.g., an antibody inhibitor of CTLA-4, PD-1, or PD-L1. In some embodiments, the antibody specifically binds a cell surface antigen, such as a tumor antigen. Exemplary tumor antigens include, but are not limited to, glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. In some embodiments, the antibody specifically binds a target antigen on a pathogenic agent, such as a bacterium or a virus.

The antibody can be an antigen-binding fragment of an antibody, e.g., a portion or fragment of an intact or complete antibody having fewer amino acid residues than the intact or complete antibody, which is capable of binding to an antigen or competing with the intact antibody (i.e., the intact antibody from which the antigen-binding fragment is derived) for binding to an antigen. Antigen-binding fragments can be prepared by recombinant DNA techniques, or by enzymatic or chemical cleavage of intact antibodies. Antigen binding fragments include, but are not limited to, Fab', F (ab')2Fv, single chain Fv (scFv), single chain Fab, diabody (diabody), single domain antibody (sdAb, nanobody), camel Ig, Ig NAR, F (ab)'3Fragment, bis-scFv, (scFv) 2Minibodies, diabodies, triabodies, tetradiabodies, disulfide stabilized Fv proteins ("dsFv"). In some embodiments, the neutralizing antibody can be a genetically engineered antibody, such as a chimeric antibody (e.g., humanized murine antibodies), heteroconjugate antibody (e.g., bispecific antibodies), or antigen-binding fragments thereof.

In some embodiments, the antibody is a neutralizing antibody that binds to a viral protein. In some embodiments, the antibody is a neutralizing antibody that binds to a receptor for a viral protein. In some embodiments, the antibody binds to a receptor that is required for viral entry into a cell (e.g., an ACE2 receptor). In some embodiments, the antibody is a neutralizing antibody (nAb) that binds to the S protein of a coronavirus and prevents or reduces its ability to infect cells. In some embodiments, the coronavirus is SARS-COV-2. In some embodiments, the nAb binds to a S protein comprising one or more mutations. In some embodiments, the nAb binds to a S protein or fragment thereof that comprises at least one point mutation in the S2 region, for example, a K986P, V987P, F817P, A892P, A899P or A942P mutation or combinations thereof. In some embodiments, the nAb binds to a S protein or fragment thereof that comprises at least one point mutation selected from A222V, E406W, K417N, K417T, N439K, L455N, E484K, Q493F, N501Y, A570D, D614G, P681H, A701V, T716I, S982A, or combinations thereof. In some embodiments the nAb is a monoclonal antibody (mAb), a functional antigen-binding fragment (Fab), a single-chain variable region fragment (scFv), or a single-domain antibody (a VHH or nanobody).

Exemplary nAbs for binding and neutralization of the S protein of SARS-COV-2 have been described, for example, in Barnes, C. O. et al. SARS-COV-2 neutralizing antibody structures inform therapeutic strategies. Nature 588, 682-687 (2020), and Chinese Patent Application No. CN111690058A, the contents of which are herein incorporated by reference in their entirety.

In some embodiments, the coding RNA sequence encodes a targeting protein that is not an antibody. Examples of non-antibody-based targeting proteins include, but are not limited to, a lipocalin, an anticalin (artificial antibody mimetic proteins that are derived from human lipocalins), "T-body", a peptide (e.g., a BICYCLE™ peptide), an affibody (antibody mimetics composed of alpha helices, e.g. an three-helix bundle), a peptibody (peptide-Fc fusion), a DARPin (designd ankyrin repeat proteins, engineered antibody mimetic proteins consisting repeat motifs), an affimer, an avimer, a knottin (a protein structural motif containing 3 disulfide bridges), a monobody, an affinity clamp, an ectodomain, a receptor ectodomain, a receptor, a cytokine, a ligand, an immunocytokine, and a centryin. See, for example, Vazquez-Lombardi, Rodrigo, et al. *Drug discovery today* 20.10 (2015): 1271-1283.

In some embodiments, the coding RNA sequence encodes a soluble receptor. Soluble receptors (sometimes referred to as soluble receptor decoys or "traps") can comprise all or a portion of the extracellular domain of a receptor protein. In some embodiments, a nucleotide sequence encoding all or a portion of the extracellular domain of a receptor protein is operably linked to a signal peptide for secretion from cells.

In some embodiments, the soluble receptor comprises an extracellular domain of a naturally occurring receptor. In some embodiments, the soluble receptor variant comprises an engineered variant of an extracellular domain of a naturally occurring receptor, such as a variant comprising one or more mutations in the extracellular domain. In some embodiments, the soluble receptor comprises one or more mutations that increase the affinity of the soluble receptor for its ligand compared to the affinity of the naturally occurring receptor for its ligand.

In some embodiments, the soluble receptor is a fusion protein comprising one or more additional protein domains operably linked to the extracellular domain of the receptor or a variant thereof. In some embodiments, the soluble receptor comprises an Fc domain of an immunoglobulin (Ig), e.g., a human immunoglobulin. In some embodiments, the soluble receptor comprises an Fc domain of a human IgG1.

In some embodiments, the soluble receptor comprises the extracellular domain of a signaling receptor, and the soluble receptor can reduce or inhibit activity of the signaling pathway by blocking binding between the endogenous receptor and its ligand.

In some embodiments, the soluble receptor is a receptor that binds to a viral protein and/or that mediates viral entry. In some embodiments, soluble receptor is a soluble ACE2 receptor. In some embodiments, the therapeutic polypeptide is a soluble ACE2 receptor variant capable of binding to an S protein of a coronavirus. In some embodiments, the soluble ACE2 receptor variant binds to the receptor binding domain (RBD) of the S protein. In some embodiments, the ACE2 receptor variant is enzymatically active. In other embodiments, the ACE2 receptor variant is enzymatically inactive. In some embodiments, the soluble ACE2 receptor variant comprises the soluble extracellular domain of wild-type (WT) human recombinant ACE2 (APN01). In some embodiments, the soluble ACE2 receptor variant comprises one or more mutations in the extracellular domain of human ACE2. In some embodiments, the soluble ACE2 receptor variant is engineered via affinity maturation to have increased binding affinity to the RBD of the S protein. Soluble ACE2 receptor variants have been described, for example in Haschke M et al., Clin Pharmacokinet. 2013 September; 52 (9): 783-92; Glasgow A et al., Proceedings of the National Academy of Sciences November 2020, 117 (45) 28046-28055; and Higuchi Y. et al., bioRxiv 2020. 09.16.299891, the contents of which are herein incorporated by reference in their entirety. In some embodiments, the soluble ACE2 receptor variant is a fusion protein, e.g., a fusion of the extracellular ACE2 receptor domain to the Fc region of the human IgG1.

In some embodiments, the coding RNA sequence encodes a functional protein. In some embodiments, the coding RNA sequence is capable of being expressed by target cells (e.g., human or mouse cells) for the production (and in certain instances, the secretion) of a functional enzyme or protein as disclosed, for example, in International Application No. PCT/US2010/058457 and WO2020237227, the contents of which are herein incorporated by reference in their entirety. In some embodiments, the therapeutic polypeptide can be engineered for secretion by operably linking a signal peptide to the amino terminus of the therapeutic polypeptide. For example, in some embodiments, upon the expression of one or more therapeutic polynucleotides by target cells, the production of a functional enzyme or protein in which a subject is deficient (e.g., a urea cycle enzyme or an enzyme associated with a lysosomal storage disorder) may be observed.

In some embodiments, the coding RNA sequence encodes a protein such as IDUA, OTC, FAH, miniDMD, DMD, p53, PTEN, COL3A1, BMPR2, AHI1, FANCC, MYBPC3, ILRG2, or ARG1, wherein deficiency of the functional protein is associated with a disease or disorder. In some embodiments, the coding RNA sequence a protein (e.g., a lysosomal enzyme) wherein deficiency of the protein is associated with a lysosomal storage disorder.

In some embodiments, the coding RNA sequence encodes a protein (e.g., an enzyme), wherein deficiency of the protein is associated with a metabolic disorder. In some embodiments, the therapeutic polypeptide comprises a urea cycle enzyme (e.g., ARG1).

In some embodiments, the coding RNA sequence encodes a protein (e.g., p53 or PTEN), wherein deficiency of the protein is associated with a cancer. In some embodiments, the therapeutic polypeptide comprises a tumor suppressor.

In some embodiments, the coding RNA sequence encodes a reporter protein, such as a fluorescent protein. Fluorescent proteins are well known to those skilled in the art, and include but are not limited to, green fluorescent proteins (GFPs), enhanced green fluorescent proteins (EGFPs), red fluorescent proteins (RFPs), and blue fluorescent proteins (BFPs).

In some embodiments, the coding RNA sequence encodes two or more polypeptides, such as two or more therapeutic polypeptides. In some embodiments, the coding RNA sequence encodes a therapeutic polypeptide and a reporter protein.

In some embodiments, the various domains or fragments in the polypeptide encoded by the coding RNA sequence may be fused to each other via a peptide linker. Flexible peptide linkers such as glycine linkers, glycine-serine linkers, and linkers containing other amino acids are known in the art (for example, suitable peptide linkers are described by Chen et al. in Fusion Protein Linkers: Property, Design and Functionality. Adv. Drug Deli Rev. 2013 Oct. 15; 65 (10): 1357-1369). Peptide linkers can also be designed by computation methods. The peptide linker can be of any length from 1 to 10, 10 to 20, 20 to 30, 30 to 40, 40 to 50, or greater than 50 amino acids.

In some embodiments, the coding RNA sequence is codon-optimized. A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

In some embodiments, the coding RNA sequence may encode or be operably linked to one or more additional elements that facilitate translation of the coding RNA sequence into a functional polypeptide. In some embodiments, the one or more additional elements are useful for monitoring translation of the coding RNA sequence.

In some embodiments, the coding RNA sequence encodes a polypeptide comprising a signal peptide (SP). In non-limiting examples, the signal peptide is the signal sequence and propeptide from human tissue plasminogen activator (tPA), the signal sequence from human IgE Immunoglobulin, or the signal peptide sequence of MHC I. In some embodiments, the signal peptide can facilitate secretion of the polypeptide encoded by the coding RNA sequence.

In some embodiments, the 3' end of the coding RNA sequence is operably linked to an in-frame 2A peptide coding sequence. In some embodiments, the coding RNA sequence does not comprise a stop codon at the 3' end. In some embodiments, the in-frame 2A peptide coding sequence replaces the stop codon. In some embodiments, the coding RNA sequence contains no stop codon and the number of nucleotides composing the coding RNA is a multiple of three. In some embodiments, the coding RNA sequence having no stop codon and the number of nucleotides composing the RNA being a multiple of three allow for rolling circle translation of the circRNA prepared using the linear RNA precursor. In some embodiments, the 2A peptide coding sequence allows for rolling circle translation of the circRNA prepared using the linear RNA precursor. In some embodiments, the 2A peptide allows cleavage of a polypeptide generated by rolling circle translation into monomeric polypeptide sequences. In non-limiting examples, the 2A peptide coding sequence encodes a P2A or T2A peptide, such as the sequence set forth in SEQ ID NO: 9 or 12.

In some embodiments, the coding RNA sequence comprises a nucleotide sequence encoding an affinity or identification tag. Exemplary tags include, but are not limited to, His tag, FLAG tag, SUMO tag, GST tag, and MBP tag.

In some embodiments, the 5' end of the coding RNA sequence is operably linked to a Kozak sequence. In some embodiments, the Kozak sequence functions as a protein translation initiation site. In some embodiments, the linear RNA comprises from the 5' end to the 3' end: a first portion of a RNA element (e.g., IRES), a Kozak sequence, a coding RNA sequence, and a second portion of the RNA element (e.g., IRES).

In some embodiments, the linear RNA further comprises a polyA or polyAC sequence disposed at the 3' end of the coding RNA sequence and at the 5' end of the second portion of the RNA element (e.g., IRES). The internal polyA sequence or polyAC spacer may range from 1 to 500 nucleotides in length (e.g., at least 20, 30, 40, 50, 60, 70, 80, 90, 120, 140, 160, 180, 200, 250, 300, 350, 400, 450, or 500 nucleotides). In some embodiments, the polyA sequence or polyAC sequence may range from 10-70, 20-60, or 30-60 nucleotides in length. In some embodiments, the linear RNA comprises no polyA sequence or polyAC sequence. Without being bound by any theory or hypothesis, an internal poly A sequence or a poly AC spacer added before IRES sequences in a circRNA can help to keep the functional second structure of IRES elements for efficient protein translation initiated by IRES. In some embodiments, the poly A sequence or poly AC spacer increases expression of the coding RNA.

II. Method of Preparing circRNAs

The present application further provides methods of preparing circRNAs using any one of the linear RNAs or constructs described in Section II above. Intramolecular ligation of a linear RNA described herein by a RNA ligase provides a circRNA comprising a RNA element and an effector RNA (e.g., coding RNA) sequence. In some embodiments, the circRNA is prepared by circularizing a linear RNA in vitro.

In some embodiments, the circRNA can be obtained by circularizing a linear RNA using a ligase such as a RNA ligase. In some embodiments, the linear RNA is circularized in vitro. In some embodiments, the linear RNA can be circularized by a T4 RNA ligase. In non-limiting examples, the linear RNA can be circularized by a ligase such as a T4 RNA ligase 1 (T4 Rnl1), and T4 RNA ligase 2 (T4 Rnl2). The linear RNAs described herein are circularized without the presence of a single stranded nucleic acid adaptor, e.g., a splint oligonucleotide.

In some embodiments, there is provided a method of preparing a circRNA, comprising: (a) contacting any one of the linear RNAs described herein with a RNA ligase under conditions that allow ligation of the nick in the linear RNA to provide a circularized RNA product; and (b) isolating the circularized RNA product, thereby providing the circRNA. In some embodiments, the ligation does not require presence of a splint oligonucleotide.

In some embodiments, the method described herein comprises circularizing a linear RNA in vitro, comprising: (a) contacting any one of the linear RNAs described herein with a RNA ligase under conditions that allow ligation of the nick in the linear RNA to provide a circularized RNA product; and (b) isolating the circularized RNA product, thereby providing the circRNA. In some embodiments, the ligation does not require presence of a splint oligonucleotide.

In some embodiments, there is provided a method of preparing a circRNA, comprising: (a) contacting any one of the linear RNAs described herein with a T4 RNA ligase 2 under conditions that allow ligation of the nick in the linear RNA to provide a circularized RNA product; and (b) isolating the circularized RNA product, thereby providing the circRNA. In some embodiments, the ligation does not require presence of a splint oligonucleotide.

A RNA ligase may be used to enzymatically link a 5'-phosphorylated end of a linear RNA described herein to the 3'-hydroxyl group of the linear RNA forming a new phosphodiester linkage. In an example reaction, a linear circular RNA is incubated at 25° C. for 8 hour with 1-10 units of T4 RNA ligase (New England Biolabs, Ipswich, Mass.) according to the manufacturer's protocol. The ligation reaction occurs without the need of a linear nucleic acid capable of basepairing with both the 5'- and 3'-region in juxtaposition that assists the enzymatic ligation reaction, i.e., the ligation is not a splint ligation.

Ligation by T4 RNA ligase 1 may lead to insertion or deletion of nucleotides at the ligation site. In some embodiments, T4 RNA ligase 2 is used to ligate the linear RNA described herein so that no additional sequences are introduced to the circRNA.

The methods described herein has high intramolecular ligation efficiency. Ligation efficiency may be assessed using known methods in the art, such as by HPLC or agarose gel electrophoresis. In some embodiments, the ligation efficiency is at least about any one of 50%, 55%, 60%, 65%, 70%, 75%, 80%, 85%, 90%, or higher. In some embodiments, the method results in less than 5%, 4%, 3%, 2%, 1% or lower amount of polymeric circRNA products, i.e., ligation of multiple copies of linear RNAs into a circular RNA.

In some embodiments, the method further comprises in vitro transcription of a nucleic acid construct encoding the linear RNA to obtain the linear RNA.

In some embodiments, the method further comprises treating the circularized RNA product with RNase R to digest the linear RNA transcripts.

In some embodiments, the method further comprises purifying the circRNA from the circRNA product. In non-limiting examples, the circRNA is purified by gel-purification or by high-performance liquid chromatography (HPLC). In some embodiments, agarose gel electrophoresis allows for simple and effective separation of circular RNA products from linear RNA precursor molecules and nicked circles. In some embodiments, the method comprises purifying the circular RNA by chromatography, such as HPLC. In some embodiments, the purified circular RNA can be stored at −80° C. In some embodiments, the step of isolating the circRNA comprises gel-purifying the circRNA. In some embodiments, the purified circRNA can be stored at −80° C.

III. Circular RNAs and Methods of Use

The present application further provides circRNAs and compositions prepared using any one of the methods of preparation, or any one of the linear RNAs or constructs described herein.

In some embodiments, the circRNA comprises an RNA element and an effector RNA sequence. In some embodiments, the effector RNA sequence is a sequence of a RNA molecule selected from the group consisting of a gRNA, a dRNA, a siRNA, a miRNA, a shRNA, a lincRNA and a coding RNA.

In some embodiments, the circRNA comprises an RNA element (e.g., an IRES) and a coding RNA sequence encoding a therapeutic polypeptides, such as an antigenic polypeptide, a functional protein, a receptor protein, or a targeting protein.

In some embodiments, the circRNA is a circRNA vaccine comprising an RNA element (e.g., an IRES) and a coding RNA sequence encoding an antigenic polypeptide. In some embodiments, the circRNA vaccine is a coronavirus vaccine, or a cancer vaccine.

In some embodiments, there is provided a cocktail composition comprising a plurality of circRNAs each comprising a coding RNA sequence encoding an antigenic polypeptide, a receptor protein of an infectious agent, or a targeting protein (e.g., an antibody such as a neutralizing antibody). In some embodiments, the plurality of circRNA encode antigenic polypeptides that are different with respect to each other, such as different mutants of an antigenic polypeptide (e.g., S protein or fragment thereof). In some embodiments, the plurality of circRNA encode receptor proteins that are different with respect to each other, such as different mutants of a receptor protein (e.g., ACE2). In some embodiments, the plurality of circRNA encode targeting proteins that are different with respect to each other, such as different antibodies (e.g., neutralizing antibodies).

The circRNAs described herein may be used to treat or prevent a disease or condition in an individual, including, but not limited to genetic diseases (e.g., hereditary genetic diseases, metabolic diseases and cancer), and infections (e.g., viral infections such as coronavirus infections). In some embodiments, the circRNA is subject to rolling circle translation by a ribosome in the individual.

In some embodiments, there is provided a method of treating or preventing a disease or condition in an individual, comprising administering to the individual an effective amount of a circRNA comprising a coding RNA sequence encoding a functional protein. In some embodiments, the functional protein is an enzyme, a receptor, a ligand, a signaling molecule, or a transcription factor. In some embodiments, the disease or condition is a metabolic disease. In some embodiments, the disease or condition is a lysosomal storage disorder. In some embodiments, the disease or condition is a cancer.

The circRNAs described herein may be used for treating a genetic disease or condition that is associated with a mutation or deficiency in a naturally-occurring protein corresponding to the therapeutic polypeptide encoded by the circRNA. In some embodiments, the disease or condition is a disease or condition associated with insufficient levels and/or activity of a naturally-occurring protein corresponding to the therapeutic polypeptide. In some embodiments, the disease or condition is a hereditary genetic disease associated with one or more mutations in naturally-occurring protein corresponding to the therapeutic polypeptide. In some embodiments, the therapeutic polypeptide is a wild-type protein, or a functional variant thereof (e.g., a functional fragment, fusion protein, or mutant).

In some embodiments, the therapeutic polypeptide can be any polypeptide that is capable of being expressed by target cells (e.g., human or mouse cells) for the production (and in certain instances, the excretion) of a functional enzyme or protein as disclosed, for example, in International Application No. PCT/US2010/058457. In some embodiments, the therapeutic polypeptide can be engineered for secretion by operably linking a signal peptide to the amino terminus of the therapeutic polypeptide. For example, in some embodiments, upon the expression of one or more therapeutic polynucleotides by target cells, the production of a functional enzyme or protein in which a subject is deficient (e.g., a urea cycle enzyme or an enzyme associated with a lysosomal storage disorder) may be observed.

Examples of disease-associated mutations that may be treated by the methods of the present application include, but are not limited to, TP53$^{W53X}$ (e.g., 158G>A) associated with cancer, IDUA$^{W402X}$ (e.g., TGG>TAG mutation in exon 9) associated with Mucopolysaccharidosis type I (MPS I), COL3A1$^{W1278X}$ (e.g., 3833G>A mutation) associated with Ehlers-Danlos syndrome, BMPR2$^{W298X}$ (e.g., 893G>A) associated with primary pulmonary hypertension, AHI1$^{W725X}$ (e.g., 2174G>A) associated with Joubert syndrome, FANCC$^{W506X}$ (e.g., 1517G>A) associated with Fanconi anemia, MYBC3$^{W1098X}$ (e.g., 3293G>A) associated with primary familial hypertrophic cardiomyopathy, and IL2RG$^{W237X}$ (e.g., 710G>A) associated with X-linked severe combined immunodeficiency. In some embodiments, the disease or condition is a cancer. In some embodiments, the disease or condition is a monogenetic disease. In some embodiments, the disease or condition is a polygenetic disease.

In some embodiments, the circRNA has a functional half-life of at least or at least about 20 hours, 24 hours, 30 hours, or 36 hours. In some embodiments, the circRNA has a duration of therapeutic effect in a human cell of at least or at least about 20 hours, 24 hours, 30 hours, or 36 hours. In some embodiments, the circRNA has a duration of therapeutic effect in a human cell greater than or equal to that of an equivalent linear RNA comprising the same expression sequence. In some embodiments, the circRNA has a functional half-life in a human cell greater than or equal to that of an equivalent linear RNA comprising the same expression sequence.

In some embodiments, there is provided a method of treating or preventing a disease or condition in an individual, comprising administering to the individual an effective amount of a circRNA vaccine comprising a coding RNA sequence encoding an antigenic polypeptide, or a cocktail composition comprising a plurality of circRNAs. In some embodiments, the antigenic polypeptide is a protein or a fragment thereof of an infectious agent, such as a virus, e.g., a coronavirus. In some embodiments, the infectious agent is SARS-COV-2.

In some embodiments, there is provided a method of treating or preventing a disease or condition in an individual, comprising administering to the individual an effective amount of a circRNA comprising a coding RNA sequence encoding a receptor protein. In some embodiments, the receptor protein is a receptor of an infectious agent, such as a virus, e.g., a coronavirus. In some embodiments, the receptor protein is a soluble receptor, such as a soluble ACE2 receptor.

In some embodiments, there is provided a method of treating or preventing a disease or condition in an individual, comprising administering to the individual an effective amount of a circRNA comprising a coding RNA sequence encoding a targeting protein, such as an antibody. In some embodiments, the targeting protein is a neutralizing antibody. In some embodiments, the targeting protein is a therapeutic antibody. In some embodiments, the targeting protein specifically binds an infectious agent, such as a virus, e.g., a coronavirus.

In some embodiments, the present application provides circRNAs for use in treating or preventing a disease or condition in an individual.

In some embodiments, the present application provides use of a circRNA comprising a nucleic acid sequence encoding a therapeutic polypeptide for the manufacture of a medicament for treating or preventing a disease or condition in an individual.

In some embodiments, the circRNA is administered as naked circRNA, or as a pharmaceutical composition comprising a transfection agent. In non-limiting examples, the transfection agent is polyethylenimine (PEI) or a lipid nanoparticle (LNP). Other examples of lipidosomes that can be used to administer the circRNA composition for administration (e.g., circRNA vaccine or pharmaceutical composition) include protamines, cationic nanoemulsions, modified dendrimer nanoparticles, protamine liposomes, cationic polymers, cationic polymer liposomes, polysaccharide particles, cationic lipid nanoparticles, cationic lipid-cholesterol nanoparticles, cationic lipid-cholesterol PEG nanoparticle, cationic lipid transfection reagents sold under the trademark LIPOFECTAMINE, nonliposomal transfection reagents sold under the trademark FUGENE, or any combination thereof can be used as the transfection agent.

In some embodiments, the liposome formulation may be influenced by, but not limited to, the selection of the cationic lipid component, the degree of cationic lipid saturation, the nature of the PEGylation, ratio of all components and biophysical parameters such as size. In some embodiments, the liposome formulation comprises a cationic lipid, a cholesterol and a PEGylated lipid. For example, a liposome formulation may comprise a cationic lipid, dipalmitoylphosphatidylcholine, cholesterol, and PEG-c-DMA. See, for example, Semple et al. Nature Biotech. 2010 28:172-176, herein incorporated by reference in its entirety. In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to RNA in liposomes may be from about 5:1 to about 20:1, from about 10:1 to about 25:1, from about 15:1 to about 30:1 and/or at least 30:1. Suitable liposome formulations have been described, for example, in WO2020237227, the contents of which are herein incorporated by reference in their entirety.

In some embodiments, the circRNA is not formulated with a transfection reagent. In some embodiments, the circRNA is delivered as naked RNA. In some embodiments, the circRNA is delivered by gene gun or by electroporation.

The circRNA composition for administration (e.g., circRNA vaccine or pharmaceutical composition) can be administered to a subject by systemic injection into the vasculature, systemic injection into the lymph nodes, subcutaneous injection or depots, or by local injection.

In some embodiments, the circRNA may be formulated in a lipid nanoparticle such as those described in International Publication No. WO2012170930, herein incorporated by reference in its entirety.

In some embodiments, the synthetic nanocarriers may be formulated for controlled and/or sustained release of the circRNA described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the circRNA may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one circRNA, which encode at least one antigen. As a nonlimiting example, the synthetic nanocarrier may include at least one antigen and an excipient for a vaccine dosage form (see International Pub No. WO2011150264 and US Pub No. US201 10293723, each of which is herein incorporated by reference in their entirety). As another non-limiting example, a vaccine dosage form may include at least two synthetic nanocarriers with the same or different antigens and an excipient (see International Pub No. WO201 1150249 and US Pub No. US201 10293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In some embodiments, the synthetic nanocarrier may comprise at least one circRNA, which encodes at least one adjuvant. As non-limiting example, the adjuvant may comprise dimethyldioctadecylammonium-bromide, dimethyldioctadecylammoniumchloride, dimethyldioctadecylammonium-phosphate or dimethyldioctadecylammoniumacetate (DDA) and an apolar fraction or part of said apolar fraction of a total lipid extract of a mycobacterium (See e.g., U.S. Pat. No. 8,241,610; herein incorporated by reference in its entirety). In another embodiment, the synthetic nanocarrier may comprise at least one circRNA and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In some embodiments, the circRNA functions as an adjuvant. As an example, RNA-sensing in the cytoplasm can trigger innate immunity, and innate immune signaling is known to contribute to adaptive immunity by diverse routes. Thus, the circRNA encoding the antigenic polypeptide or a second circRNA (e.g., a circRNA that does not encode a polypeptide) can be used as an adjuvant for boosting the adaptive immune response to the antigenic polypeptide.

In some embodiments, the circRNA compositions of the present application may be administrated with other prophylactic or therapeutic compounds. As a non-limiting example, the prophylactic or therapeutic compound may be an adjuvant or a booster. As used herein, when referring to a prophylactic composition, such as a vaccine, the term "booster" refers to an extra administration of the prophylactic composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years.

In some embodiments, the circRNA composition for administration (e.g., circRNA vaccine or pharmaceutical composition) may be administered intranasally. For example, circRNA vaccines may be administered intranasally similar to the administration of live vaccines. In some embodiments, the circRNA may be administered intramuscularly or intradermally similarly to the administration of inactivated vaccines known in the art.

In some embodiments, the circRNA vaccine comprises an adjuvant, which may enable the vaccine to elicit a higher immune response. As a non-limiting example, the adjuvant could be a sub-micron oil-in-water emulsion, which can elicit a higher immune response in human pediatric populations (see e.g., the adjuvant-containing vaccines described in US Patent Publication No. US20120027813 and US Patent No. U.S. Pat. No. 8,506,966, the contents of each of which are herein incorporated by reference in its entirety).

V. Compositions, Kits and Articles of Manufacture

Further provided by the present application are compositions comprising any one of the linear RNAs, constructs, or circRNAs described herein. In some embodiments, there is provided a pharmaceutical composition comprising any one or plurality of circRNAs described herein, and a pharmaceutically acceptable carrier. Pharmaceutical compositions can be prepared by mixing the therapeutic agents described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

The present application further provides kits and articles of manufacture for use in any one of the methods for preparing circRNAs described herein. In some embodiments, the kit comprises a linear RNA or a construct encoding the linear RNA described herein, and instructions for preparing a circRNA. In some embodiments, the kit further comprises a RNA ligase, such as T4 RNA ligase 1, or T4 RNA ligase 2. In some embodiments, the kit further comprises a reverse transcriptase.

In some embodiments, there is provided a kit comprising any one of the circRNAs described herein and instructions for treating or preventing a disease or condition (e.g., coronavirus infection or cancer). In some embodiments, the kit comprises instructions for administering the circRNA.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the circRNA as disclosed herein to provide effective treatment of an individual or of many individuals. Additionally, kits may be provided that contain sufficient dosages of the circRNA to allow for multiple administrations to an individual (e.g., initial vaccine administration and subsequent booster administration, in the case of a circRNA vaccine). Kits may also include multiple unit doses of the pharmaceutical compositions and instructions for use and packaged in quantities sufficient for storage and use in pharmacies, for example, hospital pharmacies and compounding pharmacies.

In some embodiments, the kit comprises a delivery system. The delivery system may be a unit dose delivery system. The volume of solution or suspension delivered per dose can be anywhere from about 5 to about 2000 microliters, from about 10 to about 1000 microliters, or from about 50 to about 500 microliters. Delivery systems for these various dosage forms can be syringes, dropper bottles, plastic squeeze units, atomizers, nebulizers or pharmaceutical aerosols in either unit dose or multiple dose packages. In some embodiments, there is provided a delivery system of any one of the circRNAs described herein, comprising the circRNA and a device for delivering the circRNA.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1. In Vitro circRNA Production by Ligation

Because circRNAs have no cap or poly(A) tails, Internal Ribosomal Entry Site (IRES) is required to start the translation process of circRNAs. Here we use rationally designed split IRES elements (also referred herein as "IRES splits" or "split IRES portions") to efficiently and accurately produce coding circular RNAs using a T4 RNA ligase. FIG. 1 shows an overview of the method for producing circRNAs using a construct comprising IRES splits. First, a RNA transcript (also referred to as "precursor" or "linear RNA precursor") is obtained by in vitro transcription of the construct, which contains the two IRES splits that associate with each other to form a stable intramolecular secondary structure having a nick across the two ends of the RNA transcript. The nick is subsequently ligated by a T4 RNA ligase to yield the circular RNA.

We analyzed the secondary structure of the wildtype CVB3 IRES (SEQ ID NO: 1) using RNAfold. We found that the wildtype CVB3 IRES contains highly stable double-stranded RNA structures, which may promote formation of intramolecular double strands. See, boxed region of FIG. 2A. We thus picked two sites in the double-stranded RNA regions to engineer pairs of split CVB3 IRES portions. In a first pair of CVB3 IRES splits (also referred herein as "Site 1 CVB3 IRES splits"), the 5' portion of the CVB3 IRES split (SEQ ID NO: 2) contains nucleotides 1 to 381 of the wildtype CVB3 IRES (SEQ ID NO: 1) and the first exogenous sequence GUUU. The 3' portion of the CVB3 IRES split (SEQ ID NO: 3) contains nucleotides 382 to 741 of the wildtype CVB3 IRES (SEQ ID NO: 1) and the second exogenous sequence AAAC. See, FIG. 2B. In a second pair of CVB3 IRES splits (also referred herein as "Site 2 CVB3 IRES splits"), the 5' portion of the CVB3 IRES split (SEQ ID NO: 4) contains nucleotides 1 to 342 of the wildtype CVB3 IRES (SEQ ID NO: 1) and the first exogenous sequence GUUU. The 3' portion of the CVB3 IRES split (SEQ ID NO: 5) contains nucleotides 343 to 741 of the wildtype CVB3 IRES (SEQ ID NO: 1) and the second exogenous sequence AAAC. See, FIG. 2C. To maintain the stability of the double-stranded structures, we inserted four nucleotides GUUU and its reverse complementary sequence (AAAC) immediately next to the split sites (boxed sequences in FIGS. 2B-2C).

Two constructs for producing circular RNA encoding EGFP are designed using the first pair and second pair of CVB3 IRES splits. Each construct comprises, from the 5' to the 3': a T7 promoter (SEQ ID NO: 6), the 3' portion of a CVB3 IRES split pair, EGFP-encoding sequence (SEQ ID NO: 7), a FLAG-tag encoding sequence (SEQ ID NO: 8), a P2A sequence (SEQ ID NO: 9), and the 5' portion of the CVB3 IRES split pair. The construct based on Site 1 CVB3 IRES splits (also referred herein as "Site 1 construct") has the DNA sequence of SEQ ID NO: 10. The construct based on Site 2 CVB3 IRES splits (also referred herein as "Site 2 construct") has the DNA sequence of SEQ ID NO: 11.

Figure 3:
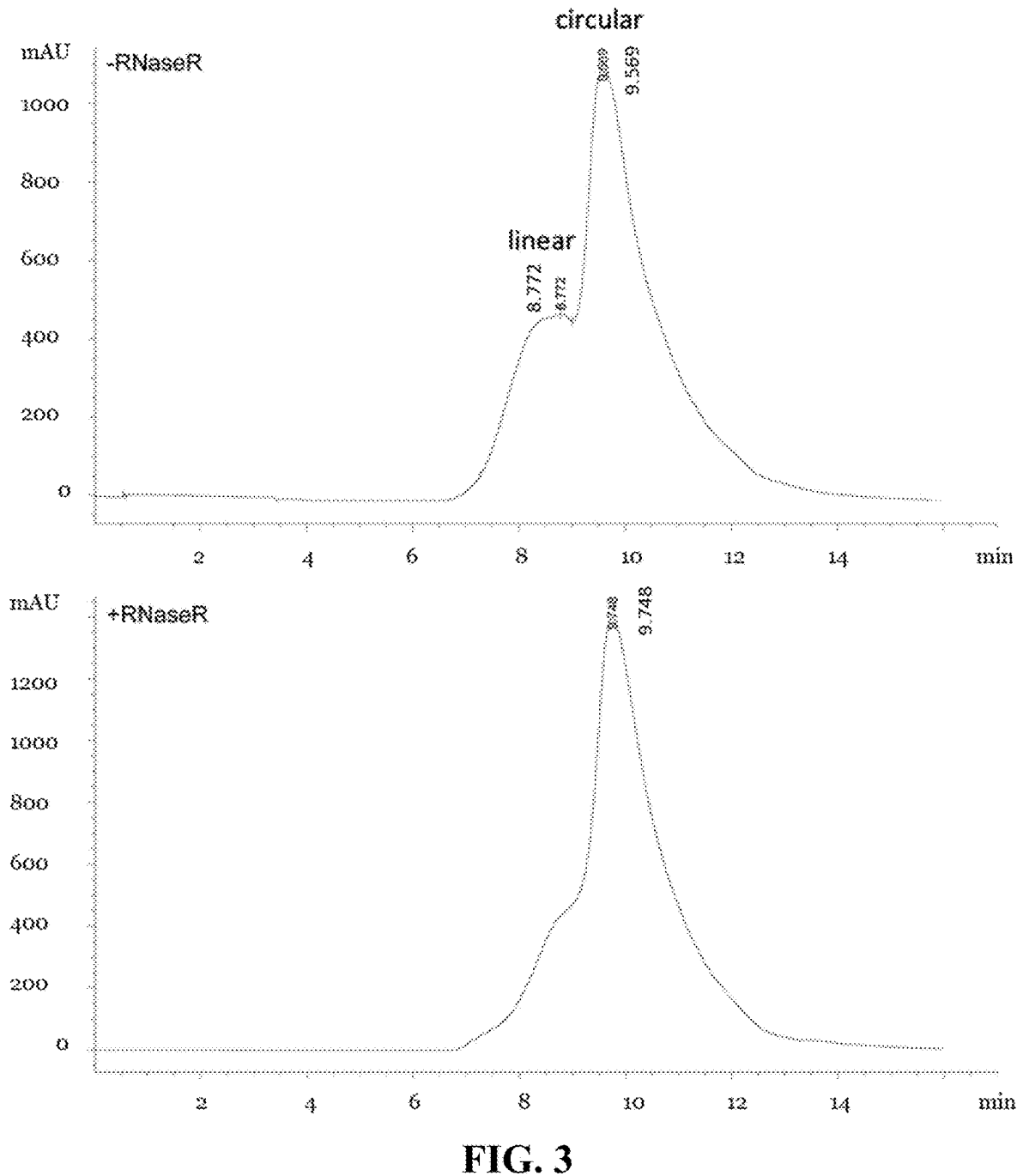
FIG. 3 shows high-performance liquid chromatography (HPLC) analysis of a circular RNA sample produced by ligation of a linear RNA transcript of a construct based on the CVB3 IRES splits of FIG. 2B (i.e., Site 1 ligation circular RNA) using T4 RNA ligase 1. In the top chromatograph, the circular RNA sample was not subject to RNAse R treatment. In the bottom chromatograph, the circular RNA sample was treated with RNAse R.

The two constructs were each subject to in vitro transcription to provide linear RNA precursors, which were ligated by T4 RNA ligase 1 or T4 RNA ligase 2 for 8 hours at 25° C. The circular RNA product from the Site 1 construct is referred herein as the Site 1 ligation circular RNA. The circular RNA product from the Site 1 construct is referred herein as the Site 2 ligation circular RNA. The ligation products were treated with RNase R to remove the linear RNA precursor. FIG. 3 shows HPLC chromatograms of a T4 RNA ligase 1-ligated Site 1 ligation circular RNA before and after RNAse R treatment. The cyclization efficiency was about 70%, and RNase R treatment degraded a lot of linear RNA products.

Figure 4A:
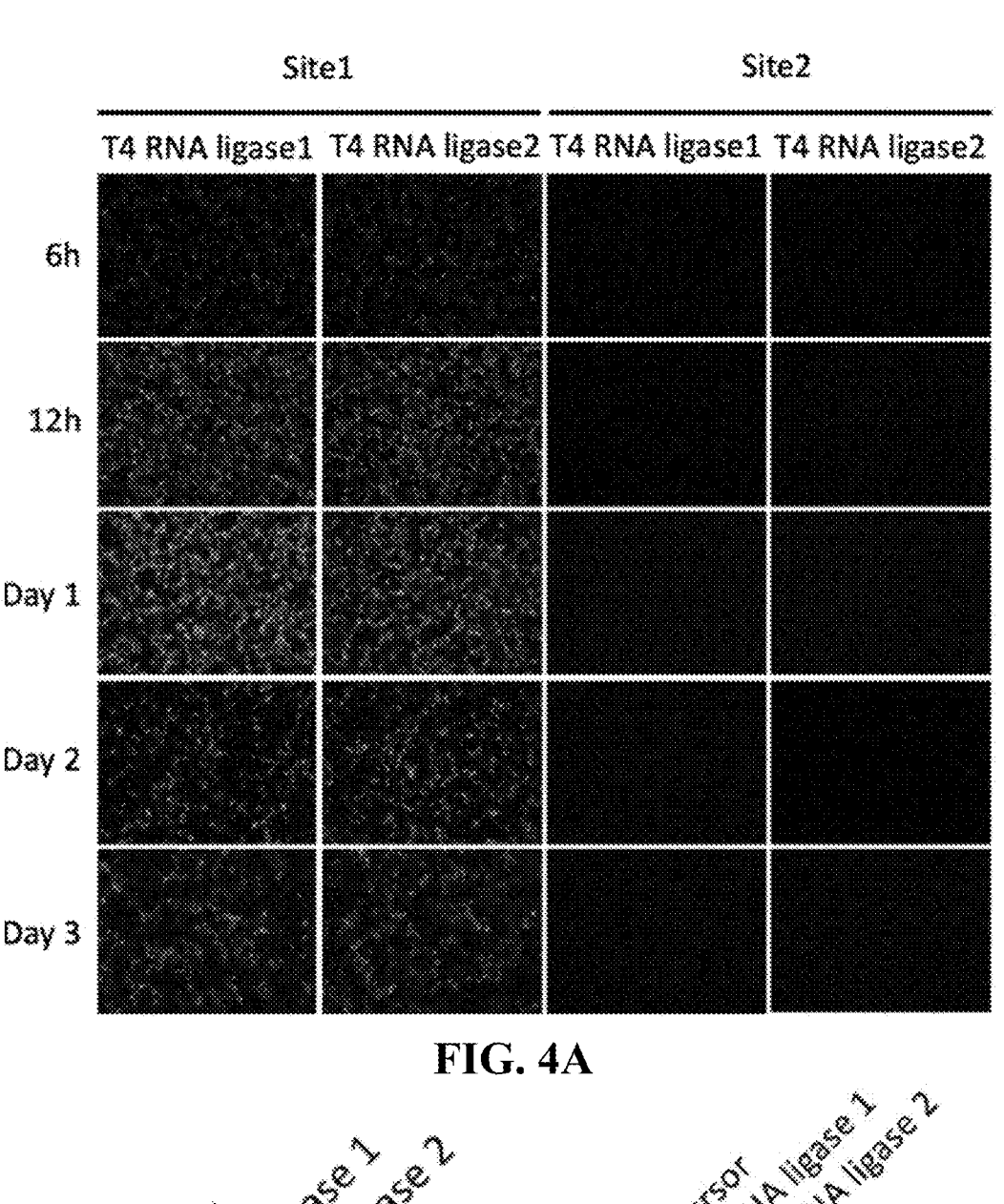
FIG. 4A shows expression EGFP in cells transfected with Site 1 and Site 2 ligated circular RNAs.

Next, we transfected each of the circular RNA products into HEK293T cells at 4 μg circRNA per well in a twelve-well plate. As shown in FIG. 4A, EGFP expression was detected in cells transfected with Site 1 ligation circular RNA, but not in cells transfected with Site 2 ligation circular RNA. We reasoned that the absence of EGFP expression may be due to disruption of functional structures of the ligated IRES in Site 2 ligation circular RNA. Western blot analysis showed that the EGFP expression level in cells transfected with Site 1 ligation circular RNA was much higher than the expression level of β-tubulin in the same cells (FIG. 4B).

Figure 5B:
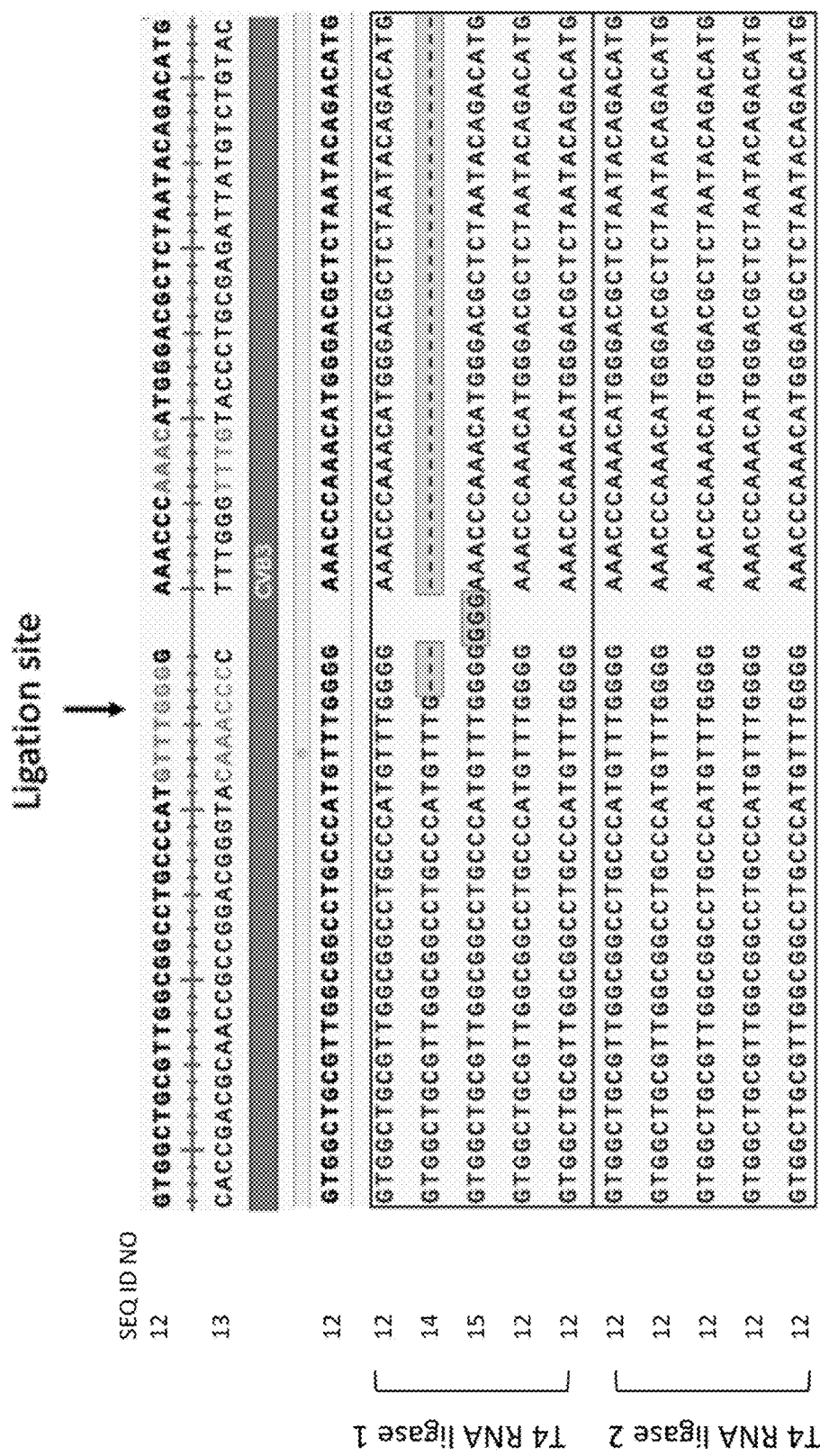
FIG. 5B shows Sanger sequencing of the ligation junction in Site 1 ligation circular RNA.

Finally, we tested whether the ligation site was accurate, i.e., free from insertion or deletion at the ligation site. We reverse transcribed the Site 1 ligation circular RNA, and PCR amplified the junction of the ligation site using forward and reverse primers as shown in FIG. 1. As shown in FIG. 5A, the PCR results confirmed that circular RNAs formed after ligation of the precursor RNA using T4 RNA ligase, while no circular RNAs were found in the precursor RNA that was not subject to T4 RNA ligase treatment. Using Sanger sequencing, we determined the sequences of the circular RNAs surrounding the ligated junction site in samples ligated by T4 RNA ligase 1 or T4 RNA ligase 2. As shown in FIG. 5B, T4 RNA ligase 2 accurately ligated the nick in the linear RNA precursor, but T4 RNA ligase 1 treatment resulted in a small number of insertions and deletions. Without being bound by theory, this may be due to the substrate requirement of T4 RNA ligase 2, which is double-stranded RNA.

```
SEQUENCE LISTING
Wildtype CVB3-IRES RNA sequence
                                              SEQ ID NO: 1
UUAAAACAGCCUGUGGGUUGAUCCCACCCACAGGCCCAUUGGGCGCUAGCACUCU

GGUAUCACGGUACCUUUGUGCGCCUGUUUUAUACCCCCUCCCCCAACUGUAACUU

AGAAGUAACACACACCGAUCAACAGUCAGCGUGGCACACCAGCCACGUUUUGAUC

AAGCACUUCUGUUACCCCGGACUGAGUAUCAAUAGACUGCUCACGCGGUUGAAGG

AGAAAGCGUUCGUUAUCCGGCCAACUACUUCGAAAAACCUAGUAACACCGUGGAA

GUUGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGGGG

AAACCCAUGGGACGCUCUAAUACAGACAUGGUGCGAAGAGUCUAUUGAGCUAGU

UGGUAGUCCUCCGGCCCCUGAAUGCGGCUAAUCCUAACUGCGGAGCACACACCCU
```

-continued

CAAGCCAGAGGGCAGUGUGUCGUAACGGGCAACUCUGCAGCGGAACCGACUACUU

UGGGUGUCCGUGUUUCAUUUUAUUCCUAUACUGGCUGCUUAUGGUGACAAUUGA

GAGAUCGUUACCAUAUAGCUAUUGGAUUGGCCAUCCGGUGACUAAUAGAGCUAU

UAUAUAUCCCUUUGUUGGGUUUAUACCACUUAGCUUGAAAGAGGUUAAAACAUU

ACAAUUCAUUGUUAAGUUGAAUACAGCAAA

5' portion of Site 1 CVB3-IRES split (contains
nucleotides 1-381 of wildtype CVB3-IRES and the
inserted first exogenous sequence, i.e. the
underlined GUUU)

SEQ ID NO: 2

UUAAAACAGCCUGUGGGUUGAUCCCACCCACAGGCCCAUUGGGCGCUAGCACUCU

GGUAUCACGGUACCUUUGUGCGCCUGUUUUAUACCCCCUCCCCCAACUGUAACUU

AGAAGUAACACACACCGAUCAACAGUCAGCGUGGCACACCAGCCACGUUUUGAUC

AAGCACUUCUGUUACCCCGGACUGAGUAUCAAUAGACUGCUCACGCGGUUGAAGG

AGAAAGCGUUCGUUAUCCGGCCAACUACUUCGAAAAACCUAGUAACACCGUGGAA

GUUGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGUUU

3' portion of Site 1 CVB3-IRES split (contains
nucleotides 382-741 of wildtype CVB3-IRES and the
inserted second exogenous sequence, i.e. the
underlined AAAC)

SEQ ID NO: 3

GGGGAAACCCAAACAUGGGACGCUCUAAUACAGACAUGGUGCGAAGAGUCUAUU

GAGCUAGUUGGUAGUCCUCCGGCCCCUGAAUGCGGCUAAUCCUAACUGCGGAGCA

CACACCCUCAAGCCAGAGGGCAGUGUGUCGUAACGGGCAACUCUGCAGCGGAACC

GACUACUUUGGGUGUCCGUGUUUCAUUUUAUUCCUAUACUGGCUGCUUAUGGUG

ACAAUUGAGAGAUCGUUACCAUAUAGCUAUUGGAUUGGCCAUCCGGUGACUAAU

AGAGCUAUUAUAUAUCCCUUUGUUGGGUUUAUACCACUUAGCUUGAAAGAGGUU

AAAACAUUACAAUUCAUUGUUAAGUUGAAUACAGCAAA

5' portion of Site 2 CVB3-IRES split (contains
nucleotides 1-342 of wildtype CVB3-IRES and the
inserted first exogenous sequence, i.e. the
underlined GUUU)

SEQ ID NO: 4

UUAAAACAGCCUGUGGGUUGAUCCCACCCACAGGCCCAUUGGGCGCUAGCACUCU

GGUAUCACGGUACCUUUGUGCGCCUGUUUUAUACCCCCUCCCCCAACUGUAACUU

AGAAGUAACACACACCGAUCAACAGUCAGCGUGGCACACCAGCCACGUUUUGAUC

AAGCACUUCUGUUACCCCGGACUGAGUAUCAAUAGACUGCUCACGCGGUUGAAGG

AGAAAGCGUUCGUUAUCCGGCCAACUACUUCGAAAAACCUAGUAACACCGUGGAA

GUUGCAGAGUGUUUCGCUCAGCACUACCCCAGUGUAGAUCAGGUCGAUGAGUCAC

CGCAUUCCCCACGUUU

3' portion of Site 2 CVB3-IRES split (contains
nucleotides 343-741 of wildtype CVB3-IRES and
the inserted nucleotide sequence, i.e. the
underlined AAAC)

SEQ ID NO: 5

GGGCGACCAAACGUGGCGGUGGCUGCGUUGGCGGCCUGCCCAUGGGGAAACCCAU

GGGACGCUCUAAUACAGACAUGGUGCGAAGAGUCUAUUGAGCUAGUUGGUAGUC

CUCCGGCCCCUGAAUGCGGCUAAUCCUAACUGCGGAGCACACACCCUCAAGCCAG

AGGGCAGUGUGUCGUAACGGGCAACUCUGCAGCGGAACCGACUACUUUGGGUGU

CCGUGUUUCAUUUUAUUCCUAUACUGGCUGCUUAUGGUGACAAUUGAGAGAUCG

-continued

UUACCAUAUAGCUAUUGGAUUGGCCAUCCGGUGACUAAUAGAGCUAUUAUAUAU

CCCUUUGUUGGGUUUAUACCACUUAGCUUGAAAGAGGUUAAAACAUUACAAUUC

AUUGUUAAGUUGAAUACAGCAAA

T7 promoter sequence
                                                        SEQ ID NO: 6
TAATACGACTCACTATA EGFP-coding DNA sequence
                                                        SEQ ID NO: 7
ATGGTGAGCAAGGGCGAGGAGCTGTTCACCGGGGTGGTGCCCATCCTGGTCGAGCT

GGACGGCGACGTAAACGGCCACAAGTTCAGCGTGTCCGGCGAGGGCGAGGGCGAT

GCCACCTACGGCAAGCTGACCCTGAAGTTCATCTGCACCACCGGCAAGCTGCCCGTG

CCCTGGCCCACCCTCGTGACCACCCTGACCTACGGCGTGCAGTGCTTCAGCCGCTAC

CCCGACCACATGAAGCAGCACGACTTCTTCAAGTCCGCCATGCCCGAAGGCTACGTC

CAGGAGCGCACCATCTTCTTCAAGGACGACGGCAACTACAAGACCCGCGCCGAGGT

GAAGTTCGAGGGCGACACCCTGGTGAACCGCATCGAGCTGAAGGGCATCGACTTCA

AGGAGGACGGCAACATCCTGGGGCACAAGCTGGAGTACAACTACAACAGCCACAA

CGTCTATATCATGGCCGACAAGCAGAAGAACGGCATCAAGGTGAACTTCAAGATCC

GCCACAACATCGAGGACGGCAGCGTGCAGCTCGCCGACCACTACCAGCAGAACACC

CCCATCGGCGACGGCCCCGTGCTGCTGCCCGACAACCACTACCTGAGCACCCAGTCC

GCCCTGAGCAAAGACCCCAACGAGAAGCGCGATCACATGGTCCTGCTGGAGTTCGT

GACCGCCGCCGGGATCACTCTCGGCATGGACGAGCTGTACAAG

FLAG tag-encoding DNA sequence
                                                        SEQ ID NO: 8
GATTACAAGGATGACGACGATAAG P2A sequence
                                                        SEQ ID NO: 9
GCTACTAACTTCAGCCTGCTGAAGCAGGCTGGAGACGTGGAGGAGAACCCTGGACC

T

Site 1 Construct (Site 1 CVB3-IRES splits
flanking EGFP-coding RNA)
                                                        SEQ ID NO: 10
TAATACGACTCACTATAGGGGAAACCCAAACATGGGACGCTCTAATACAGACATGG

TGCGAAGAGTCTATTGAGCTAGTTGGTAGTCCTCCGGCCCCTGAATGCGGCTAATCC

TAACTGCGGAGCACACACCCTCAAGCCAGAGGGCAGTGTGTCGTAACGGGCAACTC

TGCAGCGGAACCGACTACTTTGGGTGTCCGTGTTTCATTTTATTCCTATACTGGCTGC

TTATGGTGACAATTGAGAGATCGTTACCATATAGCTATTGGATTGGCCATCCGGTGA

CTAATAGAGCTATTATATATCCCTTTGTTGGGTTTATACCACTTAGCTTGAAAGAGGT

TAAAACATTACAATTCATTGTTAAGTTGAATACAGCAAAACTAGTGCCACCATGGTG

AGCAAGGGCGAGGAGCTGTTCACCGGGGTGGTGCCCATCCTGGTCGAGCTGGACGG

CGACGTAAACGGCCACAAGTTCAGCGTGTCCGGCGAGGGCGAGGGCGATGCCACCT

ACGGCAAGCTGACCCTGAAGTTCATCTGCACCACCGGCAAGCTGCCCGTGCCCTGGC

CCACCCTCGTGACCACCCTGACCTACGGCGTGCAGTGCTTCAGCCGCTACCCCGACC

ACATGAAGCAGCACGACTTCTTCAAGTCCGCCATGCCCGAAGGCTACGTCCAGGAG

CGCACCATCTTCTTCAAGGACGACGGCAACTACAAGACCCGCGCCGAGGTGAAGTT

CGAGGGCGACACCCTGGTGAACCGCATCGAGCTGAAGGGCATCGACTTCAAGGAGG

ACGGCAACATCCTGGGGCACAAGCTGGAGTACAACTACAACAGCCACAACGTCTAT

-continued

```
ATCATGGCCGACAAGCAGAAGAACGGCATCAAGGTGAACTTCAAGATCCGCCACAA

CATCGAGGACGGCAGCGTGCAGCTCGCCGACCACTACCAGCAGAACACCCCCATCG

GCGACGGCCCCGTGCTGCTGCCCGACAACCACTACCTGAGCACCCAGTCCGCCCTGA

GCAAAGACCCCAACGAGAAGCGCGATCACATGGTCCTGCTGGAGTTCGTGACCGCC

GCCGGGATCACTCTCGGCATGGACGAGCTGTACAAGGATTACAAGGATGACGACGA

TAAGGCTACTAACTTCAGCCTGCTGAAGCAGGCTGGAGACGTGGAGGAGAACCCTG

GACCTGGGTTTTTAAAACAGCCTGTGGGTTGATCCCACCCACAGGCCCATTGGGCGC

TAGCACTCTGGTATCACGGTACCTTTGTGCGCCTGTTTTATACCCCCTCCCCCAACTG

TAACTTAGAAGTAACACACACCGATCAACAGTCAGCGTGGCACACCAGCCACGTTT

TGATCAAGCACTTCTGTTACCCCGGACTGAGTATCAATAGACTGCTCACGCGGTTGA

AGGAGAAAGCGTTCGTTATCCGGCCAACTACTTCGAAAAACCTAGTAACACCGTGG

AAGTTGCAGAGTGTTTCGCTCAGCACTACCCCAGTGTAGATCAGGTCGATGAGTCAC

CGCATTCCCCACGGGCGACCGTGGCGGTGGCTGCGTTGGCGGCCTGCCCATGTTT
```

Site 2 Construct (Site 2 CVB3-IRES splits
flanking EGFP-coding RNA)
                                                              SEQ ID NO: 11
```
TAATACGACTCACTATAGGGCGACCAAACGTGGCGGTGGCTGCGTTGGCGGCCTGC

CCATGGGGAAACCCATGGGACGCTCTAATACAGACATGGTGCGAAGAGTCTATTGA

GCTAGTTGGTAGTCCTCCGGCCCCTGAATGCGGCTAATCCTAACTGCGGAGCACACA

CCCTCAAGCCAGAGGGCAGTGTGTCGTAACGGGCAACTCTGCAGCGGAACCGACTA

CTTTGGGTGTCCGTGTTTCATTTTATTCCTATACTGGCTGCTTATGGTGACAATTGAG

AGATCGTTACCATATAGCTATTGGATTGGCCATCCGGTGACTAATAGAGCTATTATA

TATCCCTTTGTTGGGTTTATACCACTTAGCTTGAAAGAGGTTAAAACATTACAATTCA

TTGTTAAGTTGAATACAGCAAAACTAGTGCCACCATGGTGAGCAAGGGCGAGGAGC

TGTTCACCGGGGTGGTGCCCATCCTGGTCGAGCTGGACGGCGACGTAAACGGCCAC

AAGTTCAGCGTGTCCGGCGAGGGCGAGGGCGATGCCACCTACGGCAAGCTGACCCT

GAAGTTCATCTGCACCACCGGCAAGCTGCCCGTGCCCTGGCCCACCCTCGTGACCAC

CCTGACCTACGGCGTGCAGTGCTTCAGCCGCTACCCCGACCACATGAAGCAGCACG

ACTTCTTCAAGTCCGCCATGCCCGAAGGCTACGTCCAGGAGCGCACCATCTTCTTCA

AGGACGACGGCAACTACAAGACCCGCGCCGAGGTGAAGTTCGAGGGCGACACCCTG

GTGAACCGCATCGAGCTGAAGGGCATCGACTTCAAGGAGGACGGCAACATCCTGGG

GCACAAGCTGGAGTACAACTACAACAGCCACAACGTCTATATCATGGCCGACAAGC

AGAAGAACGGCATCAAGGTGAACTTCAAGATCCGCCACAACATCGAGGACGGCAGC

GTGCAGCTCGCCGACCACTACCAGCAGAACACCCCCATCGGCGACGGCCCCGTGCT

GCTGCCCGACAACCACTACCTGAGCACCCAGTCCGCCCTGAGCAAAGACCCCAACG

AGAAGCGCGATCACATGGTCCTGCTGGAGTTCGTGACCGCCGCCGGGATCACTCTCG

GCATGGACGAGCTGTACAAGGATTACAAGGATGACGACGATAAGGCTACTAACTTC

AGCCTGCTGAAGCAGGCTGGAGACGTGGAGGAGAACCCTGGACCTGGGTTTTTAAA

ACAGCCTGTGGGTTGATCCCACCCACAGGCCCATTGGGCGCTAGCACTCTGGTATCA

CGGTACCTTTGTGCGCCTGTTTTATACCCCCTCCCCCAACTGTAACTTAGAAGTAACA

CACACCGATCAACAGTCAGCGTGGCACACCAGCCACGTTTTGATCAAGCACTTCTGT

TACCCCGGACTGAGTATCAATAGACTGCTCACGCGGTTGAAGGAGAAAGCGTTCGTT
```

-continued

ATCCGGCCAACTACTTCGAAAAACCTAGTAACACCGTGGAAGTTGCAGAGTGTTTCG

CTCAGCACTACCCCAGTGTAGATCAGGTCGATGAGTCACCGCATTCCCCACGTTT

T2A peptide coding sequence
                                                          SEQ ID NO: 12
GAGGGCAGAGGAAGUCUUCUAACAUGCGGUGACGUGGAGGAGAAUCCCGGCCCU

SEQ ID NO: 13
CACCGACGCAACCGCCGGACGGGTACAAACCCCTTTGGGTTTGTACCCTGCGAGATT

ATGTCTGTAC

SEQ ID NO: 14
GTGGCTGCGTTGGCGGCCTGCCCATGTTTG

SEQ ID NO: 15
GTGGCTGCGTTGGCGGCCTGCCCATGTTTGGGGGGGAAACCCAAACATGGGACGCT

CTAATACAGACATG

---

What is claimed is:

1. A linear RNA, comprising from the 5' end to the 3' end:

(a) a first portion of an RNA element;

(b) an effector RNA sequence; and (c) a second portion of the RNA element;

wherein the RNA element is an internal ribosomal entry site (IRES) or a portion thereof;

wherein the first portion of the RNA element and the second portion of the RNA element associate with each other to form a double-stranded region of at least 4 basepairs (bp) long;

wherein the 5' end of the first portion of the RNA element and the 3' end of the second portion of the RNA element form a nick in the double-stranded region; and wherein the nick can be ligated by an RNA ligase.

2. The linear RNA of claim 1, wherein the double-stranded region is about 6 bp long to about 25 bp long.

3. The linear RNA of claim 1, wherein the RNA element is at least 20 nt long.

4. The linear RNA of claim 1, wherein the double-stranded region comprises at least 2 bp 3' to the nick, and/or the double-stranded region comprises at least 2 bp 5' to the nick.

5. The linear RNA of claim 1, wherein the first portion of the RNA element and/or the second portion of the RNA element comprises a sequence that is exogenous to the reference RNA element.

6. The linear RNA of claim 1, wherein the second portion of the RNA element comprises a first exogenous sequence at the 3' end, wherein the first portion of the RNA element comprises a second exogenous sequence that is complementary of the first exogenous sequence, and wherein the first exogenous sequence and the second exogenous sequence form base pairs flanking the 5' end of the nick.

7. The linear RNA of claim 1, wherein the effector RNA sequence is a coding RNA sequence.

8. The linear RNA of claim 7, wherein the coding RNA sequence encodes a therapeutic polypeptide.

9. The linear RNA of claim 1, wherein the IRES is derived from:

(a) an IRES selected from the group consisting of Coxsackievirus B3 (CVB3) IRES, Enterovirus 71 (EV71) IRES, encephalomyocarditis virus (EMCV) IRES, picornavirus (PV) IRES, hepatitis C virus (HCV) IRES, adenovirus (AdV) IRES, human papillomavirus type 31 (HPV31) IRES, human herpesvirus (HHV) IRES, Rous sarcoma virus (RSV) IRES, and classical swine fever virus (CSFV) IRES; or (b) an IRES selected from the group consisting of FGF9 IRES, SLC7A1 IRES, and RUNX1 IRES.

10. The linear RNA of claim 9, wherein the IRES is an IRES of a CVB3 virus or a derivative thereof.

11. The linear RNA of claim 10, wherein the IRES of a CVB3 virus comprises the nucleotide sequence of SEQ ID NO: 1.

12. The linear RNA of claim 11, wherein the first portion of the RNA element comprises nucleotides 382-741 of SEQ ID NO: 1, and wherein the second portion of the RNA element comprises nucleotides 1-381 of SEQ ID NO: 1.

13. The linear RNA of claim 12, wherein the first portion of the RNA element comprises the nucleotide sequence of SEQ ID NO: 3, and wherein the second portion of the RNA element comprises the nucleotide sequence of SEQ ID NO: 2.

14. The linear RNA of claim 11, wherein the first portion of the RNA element comprises nucleotides 343-741 of SEQ ID NO: 1, and wherein the second portion of the RNA element comprises nucleotides 1-342 of SEQ ID NO: 1.

15. The linear RNA of claim 7, further comprising an in-frame 2A peptide coding sequence that is operably linked to the 3' end of the coding RNA.

16. The linear RNA of claim 1, wherein the effector RNA sequence is a sequence of a non-coding RNA selected from the group consisting of a guide RNA (gRNA), a deaminase-recruiting RNA (dRNA), a siRNA, a miRNA, a shRNA, and a long intervening non-coding (line) RNA.

17. A method of preparing a circRNA, comprising:

(a) contacting the linear RNA of claim 1 with a RNA ligase under conditions that allow ligation of the nick in the linear RNA to provide a circularized RNA product; and (b) isolating the circularized RNA product, thereby providing the circRNA.

18. A circRNA formed by ligation of the nick in the linear RNA of claim 1.

19. A nucleic acid construct comprising a nucleic acid sequence encoding the linear RNA of claim 1.

\* \* \* \* \*

SEQUENCE LISTING

Sequence total quantity: 15
SEQ ID NO: 1                    moltype = RNA   length = 741
FEATURE                         Location/Qualifiers
source                          1..741
                                mol_type = unassigned RNA
                                organism = Coxsackievirus B3
SEQUENCE: 1
ttaaaacagc ctgtgggttg atcccaccca caggcccatt gggcgctagc actctggtat  60
cacggtacct ttgtgcgcct gtttttatacc ccctcccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tggggaaacc catgggacgc tctaatacag acatggtgcg 420
aagagtctat tgagctagtt ggtagtcctc cggccctga atgcggctaa tcctaactgc 480
ggagcacaca ccctcaagcc agagggcagt gtgtcgtaac gggcaactct gcagcggaac 540
cgactacttt gggtgtccgt gtttcatttt attcctatac tggctgctta tggtgacaat 600
tgagagatcg ttaccatata gctattggat tggccatccg gtgactaata gagctattat 660
atatccctttt gttgggttta taccacttag cttgaaaag gttaaaacat tacaattcat 720
tgttaagttg aatacagcaa a                                          741

SEQ ID NO: 2                    moltype = RNA   length = 385
FEATURE                         Location/Qualifiers
misc_feature                    1..385
                                note = Synthetic Construct
source                          1..385
                                mol_type = other RNA
                                organism = synthetic construct
SEQUENCE: 2
ttaaaacagc ctgtgggttg atcccaccca caggcccatt gggcgctagc actctggtat  60
cacggtacct ttgtgcgcct gtttttatacc ccctcccccca actgtaactt agaagtaaca 120
cacaccgatc aacagtcagc gtggcacacc agccacgttt tgatcaagca cttctgttac 180
cccggactga gtatcaatag actgctcacg cggttgaagg agaaagcgtt cgttatccgg 240
ccaactactt cgaaaaacct agtaacaccg tggaagttgc agagtgtttc gctcagcact 300
accccagtgt agatcaggtc gatgagtcac cgcattcccc acgggcgacc gtggcggtgg 360
ctgcgttggc ggcctgccca tgttt                                      385

SEQ ID NO: 3                    moltype = RNA   length = 364
FEATURE                         Location/Qualifiers
misc_feature                    1..364
                                note = Synthetic Construct
source                          1..364
                                mol_type = other RNA
                                organism = synthetic construct
SEQUENCE: 3
ggggaaaccc aaacatggga cgctctaata cagacatggt gcgaagagtc tattgagcta  60
gttggtagtc ctccggcccc tgaatgcggc taatcctaac tgcggagcac acaccctcaa 120
gccagagggc agtgtgtcgt aacgggcaac tctgcagcgg aaccgactac tttgggtgtc 180
cgtgtttcat tttattccta tactggctgc ttatggtgac aattgagaga tcgttaccat 240
atagctattg gattggccat ccggtgacta atagagctat tatatatccc tttgttgggt 300
ttataccact tagcttgaaa gaggttaaaa cattacaatt cattgttaag ttgaatacag 360
caaa                                                             364

```
SEQ ID NO: 4          moltype = RNA   length = 346
FEATURE               Location/Qualifiers
misc_feature          1..346
                      note = Synthetic Construct
source                1..346
                      mol_type = other RNA
                      organism = synthetic construct
SEQUENCE: 4
ttaaaacagc ctgtgggttg atcccaccca caggcccatt gggcgctagc actctggtat   60
cacggtacct ttgtgcgcct gttttatacc ccctcccca actgtaactt agaagtaaca    120
cacaccgatc aacagtcagc gtggcacacc agccacgttt tgatcaagca cttctgttac   180
cccggactga gtatcaatag actgctcacg cggttgaagg agaaagcgtt cgttatccgg   240
ccaactactt cgaaaaacct agtaacaccg tggaagttgc agagtgtttc gctcagcact   300
accccagtgt agatcaggtc gatgagtcac cgcattcccc acgttt                  346

SEQ ID NO: 5          moltype = RNA   length = 403
FEATURE               Location/Qualifiers
misc_feature          1..403
                      note = Synthetic Construct
source                1..403
                      mol_type = other RNA
                      organism = synthetic construct
SEQUENCE: 5
gggcgaccaa acgtggcggt ggctgcgttg gcggcctgcc catggggaaa cccatgggac   60
gctctaatac agacatggtg cgaagagtct attgagctag ttggtagtcc tccggcccct   120
gaatgcggct aatcctaact gcggagcaca caccctcaag ccagagggca gtgtgtcgta   180
acgggcaact ctgcagcgga accgactact ttgggtgtcc gtgtttcatt ttattcctat   240
actggctgct tatggtgaca attgagagat cgttaccata tagctattgg attggccatc   300
cggtgactaa tagagctatt atatatccct ttgttgggtt tataccactt agcttgaaag   360
aggttaaaac attacaattc attgttaagt tgaatacagc aaa                     403

SEQ ID NO: 6          moltype = DNA   length = 17
FEATURE               Location/Qualifiers
misc_feature          1..17
                      note = Synthetic Construct
source                1..17
                      mol_type = other DNA
                      organism = synthetic construct
SEQUENCE: 6
taatacgact cactata                                                   17

SEQ ID NO: 7          moltype = DNA   length = 717
FEATURE               Location/Qualifiers
misc_feature          1..717
                      note = Synthetic Construct
source                1..717
                      mol_type = other DNA
                      organism = synthetic construct
SEQUENCE: 7
atggtgagca agggcgagga gctgttcacc ggggtggtgc ccatcctggt cgagctggac   60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaag       717

SEQ ID NO: 8          moltype = DNA   length = 24
FEATURE               Location/Qualifiers
misc_feature          1..24
                      note = Synthetic Construct
source                1..24
                      mol_type = other DNA
                      organism = synthetic construct
SEQUENCE: 8
gattacaagg atgacgacga taag                                           24

SEQ ID NO: 9          moltype = DNA   length = 57
FEATURE               Location/Qualifiers
misc_feature          1..57
                      note = Synthetic Construct
source                1..57
                      mol_type = other DNA
                      organism = synthetic construct
```

```
SEQUENCE: 9
gctactaact tcagcctgct gaagcaggct ggagacgtgg aggagaaccc tggacct        57

SEQ ID NO: 10          moltype = DNA  length = 1582
FEATURE                Location/Qualifiers
misc_feature           1..1582
                       note = Synthetic Construct
source                 1..1582
                       mol_type = other DNA
                       organism = synthetic construct
SEQUENCE: 10
taatacgact cactataggg gaaacccaaa catgggacgc tctaatacag acatggtgcg      60
aagagtctat tgagctagtt ggtagtcctc cggcccctga atgcggctaa tcctaactgc     120
ggagcacaca ccctcaagcc agagggcagt gtgtcgtaac gggcaactct gcagcggaac     180
cgactacttt gggtgtccgt gtttcatttt attcctatac tggctgctta tggtgacaat     240
tgagagatcg ttaccatata gctattggat tggccatccg gtgactaata gagctattat     300
atatcccttt gttgggttta taccacttag cttgaaaagg gttaaaacat tacaattcat     360
tgttaagttg aatacagcaa aactagtgcc accatggtga gcaagggcga ggagctgttc     420
accggggtgg tgcccatcct ggtcgagctg gacggcgacg taaacggcca caagttcagc     480
gtgtccggcg agggcgaggg cgatgccacc tacggcaagc tgaccctgaa gttcatctgc     540
accaccggca agctgcccgt gccctggccc accctcgtga ccaccctgac ctacggcgtg     600
cagtgcttca gccgctaccc cgaccacatg aagcagcacg acttcttcaa gtccgccatg     660
cccgaaggct acgtccagga gcgcaccatc ttcttcaagg acgacggcaa ctacaagacc     720
cgcgccgagg tgaagttcga gggcgacacc ctggtgaacc gcatcgagct gaagggcatc     780
gacttcaagg aggacggcaa catcctgggg cacaagctgg agtacaacta caacagccac     840
aacgtctata tcatggccga caagcagaag aacggcatca ggtgaactt caagatccgc      900
cacaacatcg aggacggcag cgtgcagctc gccgaccact accagcagaa cacccccatc     960
ggcgacggcc ccgtgctgct gcccgacaac cactacctga gcacccagtc cgccctgagc    1020
aaagacccca acgagaagcg cgatcacatg gtcctgctgg agttcgtgac cgccgccggg    1080
atcactctcg gcatggacga gctgtacaag gattacaagg atgacgacga taaggctact    1140
aacttcagcc tgctgaagca ggctggagac gtggaggaga accctggacc tgggttttta    1200
aaacagcctg tgggttgatc ccacccacag gcccattggg cgctagcact ctggtatcac    1260
ggtacctttg tgcgcctgtt ttataccccc tcccccaact gtaacttaga agtaacacac    1320
accgatcaac agtcagcgtg gcacaccagc cacgttttga tcaagcactt ctgttacccc    1380
ggactgagta tcaatagact gctcacgcgg ttgaaggaga aagcgttcgt tatccggcca    1440
actacttcga aaaacctagt aacaccgtgg aagttgcaga gtgtttcgct cagcactacc    1500
ccagtgtaga tcaggtcgat gagtcaccgc attccccacg ggcgaccgtg gcggtggctg    1560
cgttggcggc ctgcccatgt tt                                             1582

SEQ ID NO: 11          moltype = DNA  length = 1582
FEATURE                Location/Qualifiers
misc_feature           1..1582
                       note = Synthetic Construct
source                 1..1582
                       mol_type = other DNA
                       organism = synthetic construct
SEQUENCE: 11
taatacgact cactataggg cgaccaaacg tggcggtggc tgcgttggcg gcctgcccat      60
ggggaaaccc atgggacgct ctaatacaga catggtgcga agagtctatt gagctagttg     120
gtagtcctcc ggcccctgaa tgcggctaat cctaactgcg gagcacacac cctcaagcca     180
gagggcagtg tgtcgtaacg ggcaactctg cagcggaacc gactactttg ggtgtccgtg     240
tttcatttta ttcctatact ggctgcttat ggtgacaatt gagagatcgt taccatatag     300
ctattggatt ggccatccgg tgactaatag agctattata tatccctttg ttgggtttat     360
accacttagc ttgaaagagg ttaaaacatt acaattcatt gttaagttga atacagcaaa     420
actagtgcca ccatggtgag caagggcgag gagctgttcc cggggtggt gcccatcctg      480
gtcgagctgg acggcgacgt aaacggccac aagttcagcg tgtccggcga gggcgagggc     540
gatgccacct acggcaagct gaccctgaag ttcatctgca ccaccggcaa gctgcccgtg     600
ccctggccca ccctcgtgac caccctgacc tacggcgtgc agtgcttcag ccgctacccc     660
gaccacatga agcagcacga cttcttcaag tccgccatgc ccgaaggct acgtccagga      720
gcgcaccatc ttcttcaagg acgacggcaa ctacaagacc gcgccgaggt gaagttcga      780
ggcgacaccc tggtgaaccg catcgagctg aagggcatcg acttcaagga ggacggcaac     840
atcctggggc acaagctgga gtacaactac aacagccaca cgtctatat catggccgac      900
aagcagaaga acggcatcaa ggtgaacttc aagatccgcc acaacatcga ggacggcagc     960
gtgcagctcg ccgaccacta ccagcagaac acccccatc gcgacggcc cgtgctgct      1020
cccgacaacc actacctgag cacccagtcc gccctgagca agaccccaa cgagaagcgc     1080
gatcacatgg tcctgctgga gttcgtgacc gccgccggga tcactctcgg catggacgag    1140
ctgtacaagg attacaagga tgacgacgat aaggctacta acttcagcct gctgaagcag    1200
gctggagacg tggaggagaa ccctggacct gggttttta aacagcctgt gggttgatcc     1260
cacccacagg cccattgggc gctagcactc tggtatcacg gtacctttgt gcgcctgttt    1320
tataccccct cccccaactg taacttagaa gtaacacaca ccgatcaaca gtcagcgtgg    1380
cacaccagcc acgttttgat caagcacttc tgttaccccg gactgagtat caatagactg    1440
ctcacgcggt tgaaggagaa agcgttcgtt atccggccaa ctacttcgaa aaacctagta    1500
acaccgtgga agttgcagag tgtttcgctc agcactaccc cagtgtagat caggtcgatg    1560
agtcaccgca ttccccacgt tt                                             1582

SEQ ID NO: 12          moltype = RNA  length = 54
FEATURE                Location/Qualifiers
misc_feature           1..54
                       note = Synthetic Construct
```

-continued

```
source                    1..54
                          mol_type = other RNA
                          organism = synthetic construct
SEQUENCE: 12
gagggcagag gaagtcttct aacatgcggt gacgtggagg agaatcccgg ccct        54

SEQ ID NO: 13             moltype = DNA  length = 67
FEATURE                   Location/Qualifiers
misc_feature              1..67
                          note = Synthetic Construct
source                    1..67
                          mol_type = other DNA
                          organism = synthetic construct
SEQUENCE: 13
caccgacgca accgccggac gggtacaaac ccctttgggt ttgtaccctg cgagattatg  60
tctgtac                                                            67

SEQ ID NO: 14             moltype = DNA  length = 30
FEATURE                   Location/Qualifiers
misc_feature              1..30
                          note = Synthetic Construct
source                    1..30
                          mol_type = other DNA
                          organism = synthetic construct
SEQUENCE: 14
gtggctgcgt tggcggcctg cccatgtttg                                   30

SEQ ID NO: 15             moltype = DNA  length = 70
FEATURE                   Location/Qualifiers
misc_feature              1..70
                          note = Synthetic Construct
source                    1..70
                          mol_type = other DNA
                          organism = synthetic construct
SEQUENCE: 15
gtggctgcgt tggcggcctg cccatgtttg gggggaaac ccaaacatgg gacgctctaa   60
tacagacatg                                                         70
```